(12) United States Patent
Li et al.

(10) Patent No.: US 11,384,062 B2
(45) Date of Patent: Jul. 12, 2022

(54) DEUTERATED (S)-2-(4-(PIPERIDIN-3-YL)PHENYL)-2H-INDAZOLE-7-CARBOXAMIDE

(71) Applicant: CombiPhos Catalysts, Inc., Hamilton, NJ (US)

(72) Inventors: George Y. Li, Belle Mead, NJ (US); Bin Tao, Pennington, NJ (US); Duanjie Hou, Trenton, NJ (US)

(73) Assignee: CombiPhos Catalysts, Inc., Hamilton, NJ (US)

(*) Notice: Subject to any disclaimer, the term of this patent is extended or adjusted under 35 U.S.C. 154(b) by 147 days.

(21) Appl. No.: 16/603,202

(22) PCT Filed: Mar. 31, 2018

(86) PCT No.: PCT/US2018/025601
§ 371 (c)(1),
(2) Date: Oct. 4, 2019

(87) PCT Pub. No.: WO2018/187187
PCT Pub. Date: Oct. 11, 2018

(65) Prior Publication Data
US 2021/0300895 A1 Sep. 30, 2021

Related U.S. Application Data

(60) Provisional application No. 62/481,144, filed on Apr. 4, 2017.

(51) Int. Cl.
*C07D 401/10* (2006.01)
*A61K 9/00* (2006.01)

(52) U.S. Cl.
CPC .......... *C07D 401/10* (2013.01); *A61K 9/0053* (2013.01); *C07B 2200/05* (2013.01)

(58) Field of Classification Search
CPC ............. C07D 401/10; A61K 9/0053; C07B 2200/05; C07B 59/002; A61P 35/00
USPC ........................................................ 514/322
See application file for complete search history.

(56) References Cited

U.S. PATENT DOCUMENTS

| | | | |
|---|---|---|---|
| 6,334,997 B1 * | 1/2002 | Foster | C07B 59/002 424/1.81 |
| 8,071,623 B2 * | 12/2011 | Jones | A61P 9/00 514/322 |
| 8,436,185 B2 * | 5/2013 | Foley | A61P 9/00 546/199 |
| 9,023,868 B2 * | 5/2015 | Czarnik | A61K 31/454 514/323 |
| 9,145,390 B2 * | 9/2015 | Pandya | A61K 31/44 |
| 2004/0253180 A1 * | 12/2004 | Foster | C07B 59/002 424/9.2 |
| 2010/0286203 A1 | 11/2010 | Foley et al. | |

(Continued)

FOREIGN PATENT DOCUMENTS

| | | |
|---|---|---|
| WO | 2007/113596 A1 | 10/2007 |
| WO | 2008/084261 A1 | 7/2008 |
| WO | 2009/087381 A1 | 7/2009 |

OTHER PUBLICATIONS

Fischer et al., "The complexities, etc.," Current Opinion in Drug Discovery & Development 2006, 9(1), 101-109.*

(Continued)

*Primary Examiner* — Taylor V Oh
(74) *Attorney, Agent, or Firm* — Hojka Qadeer, LLC

(57) ABSTRACT

A deuterated compound having the structure of Formula I: or a pharmaceutically acceptable salt, solvate, or prodrug thereof; or a salt of a prodrug thereof; or a hydrate or polymorph thereof; wherein $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ are selected from the group consisting of hydrogen or deuterium, wherein at least one of $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ is deuterium; and wherein each carbon is independently optionally replaced with $^{13}C$ is disclosed herein. Pharmaceutical compositions comprising the compounds of Formula (I) and the use of the compounds as inhibitors of the enzyme poly ADP ribose polymerase (PARP) for the treatment of patients with BRCA-mutation positive ovarian cancer and BRCA-positive breast cancer is also disclosed herein.

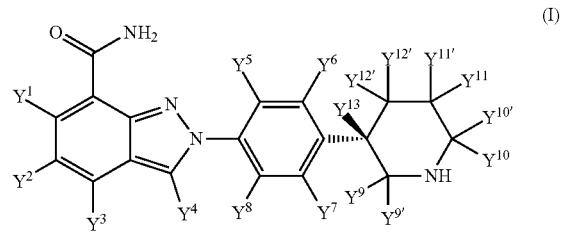

(I)

19 Claims, No Drawings

(56) References Cited

U.S. PATENT DOCUMENTS

2012/0302605 A1   11/2012   DeWitt
2014/0005211 A1    1/2014   Pandya et al.
2014/0142141 A1    5/2014   Czarnik
2017/0015670 A1    1/2017   Tung et al.

OTHER PUBLICATIONS

Wade, "Deuterium isotope, etc.," Chemico-Biological Interactions 117 (1999) 191-217.*
Foster, Deuterium Isotope, etc., TIPD, Dec. 1984, 524-527.*
Blake, Studies with, etc., J of Pharmaceutical Sciences, 64(3), 1975, 367-391.*
Dorwald, Side Reactions in Organic Synthesis 2005, Wiley:VCH Weinheim Preface, pp. 1-15 & Chapter *, pp. 279-308.*
Fisher, M. B., et al. "The Complexities Inherent in Attempts to Decrease Drug Clearance by Blocking Sites of CYP-Mediated Metabolism," Curr. Opin. Drug Discov. Dev. 2006, 9(1), 101-09.
Howland, R. H., "Deuterated Drugs," J. Psychosoc. Nurs. Ment. Health Serv., 2015, 53(9), 13-16.
Nikolaides, L., "PARP Inhibitor Approved as Maintenance for Recurrent Ovarian Cancer," Oncology Practice, 2017, 1-5, available at: https://www.mdedge.com/oncologypractice/article/134429/gynecologic-cancer/parp-inhibitor-approved-maintenance-recurrent.
Wako Organic Square, Japan, 2010, 33, 1-21.

* cited by examiner

DEUTERATED (S)-2-(4-(PIPERIDIN-3-YL)PHENYL)-2H-INDAZOLE-7-CARBOXAMIDE

CROSS-REFERENCE TO RELATED APPLICATIONS

This application claims priority to U.S. Provisional Patent Application Ser. No. 62/481,144, filed on Apr. 4, 2017, the disclosure of which is incorporated herein in its entirety by reference.

BACKGROUND

Field of the Invention

The present disclosure relates to isotopologues of niraparib, where one or more hydrogen atoms are substituted with deuterium.

Description of the Related Art

Niraparib, or (S)-2-(4-(piperidin-3-yl)phenyl)-2H-indazole-7-carboxamide, is shown below:

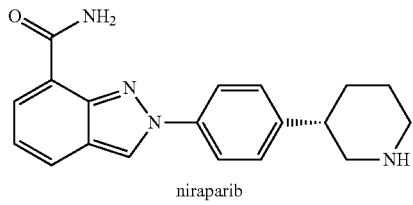 [SMILES: NC(=O)c1cccc2cn(-c3ccc([C@@H]4CCCNC4)cc3)nc12]

niraparib

Niraparib, and salts, solvates, hydrates, and polymorphs thereof, are known as PARP inhibitors (inhibitors of poly ADP ribose polymerase). Niraparib and pharmaceutical compositions comprising the same have utility in the treatment of a BRCA-mutation positive ovarian cancer and BRCA-positive breast cancer. Definitions and descriptions of these conditions are known to the skilled practitioner and are further delineated in various patents and patent applications and references contained therein. See also *Harrison's Principles of Internal Medicine* 16th Edition, Kasper, D. L., et. al. Eds., 2004, McGraw-Hill Professional; *Robbins & Cotran Pathologic Basis of Disease*, Kumar, V. et. al. Eds., 2004, W. B. Saunders.

Niraparib, previously known as MK-4827, is an inhibitor of poly ADP ribose polymerase (PARP) enzymes, including $PARP_1$, $PARP_2$ and $PARP_3$. PARP enzymes are involved in normal cellular homeostasis, such as DNA transcription, cell cycle regulation, and DNA repair. Niraparib is a useful agent for the treatment of cancers in people with hereditary BRCA-1 or BRCA-2 mutations, including various ovarian, breast, and prostate cancers. BRCA-1 or BRCA-2 mutations may cause a genetic predisposition to the development of some forms of cancer and may be resistant to many forms of cancer treatment. However, cancer cells of this type have an increased reliance on PARP to repair the cellular DNA and enable the cancer cells to continue dividing, and thus may be particularly vulnerable to PARP inhibitors. Thus, agents selectively inhibiting PARP may be of benefit for the treatment of such cancers.

Niraparib has shown excellent $PARP_1$ and $PARP_2$ inhibition activity, with $IC_{50}$ values of 3.8 nM and 2.1 nM, respectively. In a whole cell assay, niraparib inhibits PARP activity, with an $EC_{50}$ value of 4 nM, and inhibits the proliferation of cancer cells with mutant BRCA-1 and BRCA-2, with $CC_{50}$ in the 10-100 nM range.

Niraparib demonstrates efficacy in vivo as a single agent in a mouse xenograft model of BRCA-1 deficient cancer. At 80 mg/kg (qd, oral dosing), a significant inhibition of tumor growth was observed after only one or two weeks of treatment. Continuous daily dosing for three or four weeks was more efficacious and induced tumor shrinkage, with complete and sustained regression observed after four week treatment. Niraparib was also shown to be active in a CAPAN-1 pancreatic cancer cell xenograft model, with ~60% tumor growth inhibition at 80 mg/kg (qd, oral dosing) for two, three, or four weeks. In addition, it strongly enhances the effect of radiation on a variety of human tumor xenografts, both p53 wild type and p53 mutant. Enhancement of radiation response is observed in clinically relevant radiation-dose fractionation schedules. See Jones, P. et al. "Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and -2 Mutant Tumors," *J. Med. Chem.* 2009, 52, 7170-7185; Jones, P. et al. "Niraparib: A Poly(ADP-ribose) Polymerase (PARP) Inhibitor for the Treatment of Tumors with Defective Homologous Recombination," *J. Med. Chem.* 2015, 58, 3302-3314.

In a Phase 3 trial (NOVA) with 500 enrolled patients with recurrent ovarian cancer following platinum-based chemotherapy, niraparib significantly achieved its primary endpoint of progression-free survival (PFS) in the germline BRCA mutant patients, with a hazard ratio of 0.27. The median PFS for patients treated with niraparib was 21.0 months, compared to 5.5 months for the control. This trial also successfully achieved its primary endpoint of PFS in non-gBRCAmut cohort for patients with HRD (homologous recombination deficient)-positive tumors, with a hazard ratio of 0.38. The median PFS for patients with HRD-positive tumors treated with niraparib was 12.9 months, compared to 3.8 months for the control. Niraparib also showed statistical significance in the overall non-germline BRCA mutant cohort, which included patients with both HRD-positive and HRD-negative tumors, with a hazard ratio of 0.45. The median PFS for patients treated with niraparib was 9.3 months, compared to 3.9 months for the control. See Nasdaq GlobeNewswire, "TESARO's Niraparib Significantly Improved Progression-Free Survival for Patients With Ovarian Cancer in Both Cohorts of the Phase 3 NOVA Trial," Jun. 29, 2016, Waltham, Mass. (available at globenewswire.com/news-release/2016/06/29/852247/0/en/TESARO-s-Niraparib-Significantly-Improved-Progression-Free-Survival-for-Patients-With-Ovarian-Cancer-in-Both-Cohorts-of-the-Phase-3-NOVA-Trial.html).

Currently ongoing studies of niraparib include a Phase 2 trial in patients with ovarian cancer (the QUADRA trial), a Phase 3 trial for the treatment of patients with BRCA-positive breast cancer (the BRAVO trial), and a Phase 3 trial in patients with first-line ovarian cancer (the PRIMA trial). Several combination studies are also underway, including trials of niraparib in combination with pembrolizumab, bevacizumab, and temozolomide. See Nasdaq GlobeNewswire, "TESARO Provides Pipeline Update at ASCO Investor Briefing," Jun. 4, 2016 (available at ir.tesarobio.com/news-releases/news-release-details/tesaro-provides-pipeline-update-asco-investor-briefing).

The most common (≥10%) treatment-emergent grade 3/4 adverse events were thrombocytopenia (28.3%), anemia (24.8%), and neutropenia (11.2%). The discontinuation rate was 14.7% for niraparib treated patients and 2.2% for the control. See Nasdaq GlobeNewswire, "TESARO's Niraparib Significantly Improved Progression-Free Survival for Patients With Ovarian Cancer in Both Cohorts of the Phase 3 NOVA Trial," Jun. 29, 2016, Waltham, Mass. (available at globenewswire.com/news-release/2016/06/29/852247/0/en/TESARO-s-Niraparib-Significantly-Improved-Progression-Free-Survival-for-Patients-With-Ovarian-Cancer-in-Both-Cohorts-of-the-Phase-3-NOVA-Trial.html).

Thus there remains an unmet clinical need for a method of administering higher doses of niraparib to patients in a manner that eliminates or minimizes adverse events, such as thrombocytopenia, anemia, and neutropenia, and other potentially dangerous side effects that may occur with niraparib therapy. A compound displaying the beneficial activities of niraparib with a decreased metabolic liability that further extends its effective pharmacological life by increasing the concentration of the agent in the blood and improving the effective bioavailability will lead to a lower required dosage, thereby reducing the potential toxicity and other side effects.

SUMMARY

A deuterated compound having the structure of Formula I:

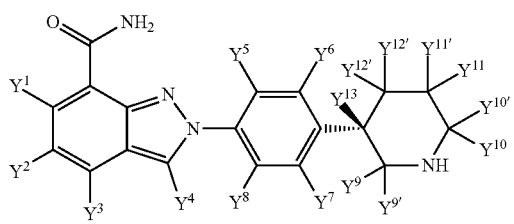

or a pharmaceutically acceptable salt, solvate, or prodrug thereof; or a salt of a prodrug thereof; or a hydrate or polymorph thereof;

wherein $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ are selected from the group consisting of hydrogen or deuterium, wherein at least one of $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ is deuterium; and wherein each carbon is independently optionally replaced with $^{13}C$ is disclosed herein.

The disclosed niraparib isotopologues are PARP inhibitors and possess unique biopharmaceutical and metabolic properties as compared to niraparib. The disclosed compounds may also be used to accurately determine the concentration of niraparib in biological fluids and to determine metabolic patterns of niraparib and its isotopologues. Compositions comprising the disclosed compounds and methods for treating BRCA-mutation positive ovarian cancer and BRCA-positive breast cancer, alone or in combination with additional agents, are also disclosed herein.

Without being bound by any theory of operation, it is believed that niraparib may be primarily metabolized by CYP3A and other drug metabolizing enzymes. The primary metabolic pathways for niraparib may involve oxidation, presumably at the benzylic carbon and/or at the electron rich nitrogen and/or α-carbons of the piperidine ring, including N-oxidation, oxidative N-dealkylation, ring oxidation, and ring opening. A radiolabeled disposition study with [$^{14}C$]-niraparib dosed IV to bile duct cannulated rats has found numerous metabolites, along with 45% of recovered radioactivity as the parent drug. See Jones, P. et al. "Niraparib: A Poly(ADP-ribose) Polymerase (PARP) Inhibitor for the Treatment of Tumors with Defective Homologous Recombination," *J. Med. Chem.* 2015, 58, 3302-3314.

Limiting the production of these metabolites has the potential to decrease the danger of the administration of niraparib and related drugs and may even allow increased dosage and concomitant increased efficacy. All of these transformations may occur through polymorphically-expressed enzymes, thus exacerbating the interpatient variability. For all of the foregoing reasons, there is a strong likelihood that a drug with a longer half-life will diminish the aforementioned problems and result in greater efficacy and cost savings.

Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, and/or (f) decrease the production of deleterious metabolites in specific tissues and/or create a more effective drug and/or a safer drug for both intentional and unintentional polypharmacy. Deuteration offers a strong potential to slow drug metabolism via various oxidative and other modification mechanisms. In particular, deuteration of drugs produces benefits when using combinations of different medications, which is common for patients suffering from cancer.

The disclosed compounds and compositions are also useful as analytical reagents for determining the concentration of niraparib in solution. As used herein, niraparib refers to the compound wherein all hydrogen atoms and all carbon atoms are present at the approximate percentages of their natural isotopic abundance. While some variation of natural isotopic abundance does occur depending upon the origin of chemical starting materials and reagents, the concentration of naturally abundant stable hydrogen and carbon isotopes, notwithstanding this variation, is small and immaterial with respect to the degree of stable isotopic substitution of compounds disclosed herein. See, e.g., Wada, E. et al. *Seikagaku*, 1994 66, 15; Ganes, L. Z. et al. *Comp. Biochem. Physiol. A Mol. Integr. Physiol.* 1998, 119, 725.

The altered properties of the disclosed compounds will not significantly affect their ability to bind to their protein target. This is because such binding is primarily dependent upon non-covalent binding between the protein and the inhibitor, and may be impacted both positively and negatively by isotopic substitution depending on the specific substitution involved, and any negative effects that a heavier atom in the disclosed compounds may have on the highly optimized non-covalent binding between the disclosed compounds and their targeted proteins will be relatively minor. Major factors contributing to the noncovalent recognition of small molecules by proteins and the binding strength between them include Van der Waals forces, hydrogen bonds, ionic bonds, molecular reorganization, desolvation energy of the small molecule, hydrophobic interactions, and, in some situations, displacement energy for pre-existing bound ligands. See, e.g., *Goodman & Gilman's The Pharmacological Basis of Therapeutics, Tenth Edition*, Hardman, J. G. et al., Eds. 2001, McGraw-Hill; *The Organic Chemistry of Drug Design and Drug Action*, Silverman, R. B., 2004, Academic Press.

The disclosed compounds possess molecular topologies very similar to niraparib, as the exchange of deuterium for hydrogen does not appreciably alter molecular configuration, and the exchange of $^{13}C$ for $^{12}C$ is conformationally neutral. See Holtzer, M. E. et al. *Biophys J.* 2001, 80, 939. Deuterium replacement does cause a slight decrease in Van der Waals radius, see Wade, D. *Chem. Biol. Interact.* 1999, 117, 191, but such decrease will likely not appreciably reduce the binding affinity between the disclosed compounds and their receptors as compared to niraparib. Further, the slightly smaller size of the disclosed deuterated compounds prevents additional undesirable steric interactions with the binding protein as compared to niraparib.

Neither deuterium nor $^{13}C$ atoms in the disclosed compounds contribute significantly to hydrogen bonding or ionic interactions with the protein receptors. This is because the major hydrogen bond and ionic interactions formed by niraparib with its targeted proteins are mediated by the oxygens, nitrogens, and the amine-bound hydrogens within niraparib. Any deuterium atoms attached to the amine nitrogen will be rapidly exchanged with bulk solvent protons under physiological conditions. Protein reorganization or side chain movement will be identical between the disclosed compounds and niraparib. Desolvation energy of the disclosed compounds will be equivalent to or less than that of niraparib, resulting in neutral or increased binding affinity for the receptor. See Turowski, M. et al. *J. Am. Chem. Soc.* 2003, 125, 13836. The replacement of $^{12}C$ by $^{13}C$ in the disclosed compounds will also cause no significant change in desolvation energy. Thus, the disclosed compounds will advantageously retain substantial PARP inhibitory activity with a reduced rate of metabolite generation.

The disclosed compounds and compositions are also useful as analytical reagents for determining the concentration of niraparib in solution.

DETAILED DESCRIPTION OF THE
ILLUSTRATED EMBODIMENTS

A deuterated compound having the structure of Formula I:

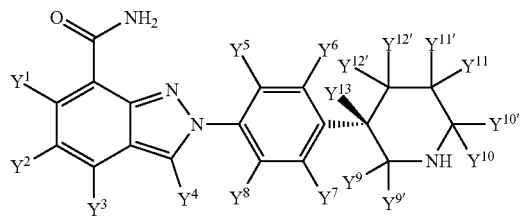

or a pharmaceutically acceptable salt, solvate, or prodrug thereof; or a salt of a prodrug thereof; or a hydrate or polymorph thereof;

wherein $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ are selected from the group consisting of hydrogen or deuterium, wherein at least one of $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ is deuterium; and wherein each carbon may be independently optionally replaced with $^{13}C$ is disclosed herein.

As used herein, where a specific atom $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$, in the disclosed compounds of formula (I) is described as being deuterium, this means that:

the compound incorporates at least 5% deuterium in at least one of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ identified as being deuterium;

preferably at least about 10% deuterium in at least one of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ identified as being deuterium;

more preferably at least 20% deuterium in at least one of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ identified as being deuterium;

even more preferably at least 50% deuterium in at least one of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ identified as being deuterium;

even more preferably at least 70% deuterium in at least one of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ identified as being deuterium;

even more preferably at least 80% deuterium in at least one of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ identified as being deuterium;

even more preferably at least 90% deuterium in at least one of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ identified as being deuterium; and most preferably at least 98% deuterium in at least one of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ identified as being deuterium for best results;

wherein the description that the compound incorporates at least a specific percentage of deuterium in at least one of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ described as being deuterium means that the deuterium is observable or is specifically identifiable as not being observed on an analytically measurable timescale, such as via nuclear magnetic resonance (NMR) spectroscopy.

As used herein, where a specific atom $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ in the disclosed compounds of formula (I) is described as being hydrogen, this means that:

the compound incorporates at least 95% hydrogen in all of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ identified as being hydrogen;

wherein the description that the compound incorporates at least a specific percentage of hydrogen in all of the positions $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, or $Y^{13}$ described as being hydrogen means that the hydrogen is observable, specifically identifiable as not being observed, or otherwise specifically identifiable as not capable of being observed on an analytically measurable timescale, such as via nuclear magnetic resonance (NMR) spectroscopy.

The deuterated compounds of formula (I) disclosed herein may also contain less prevalent isotopes for other elements, including but not limited to $^{13}C$ or $^{14}C$ substitution for carbon, $^{15}N$ substitution for nitrogen, and $^{17}O$ or $^{18}O$ substitution for oxygen.

As used herein, the term "compound" includes salts, prodrugs, and prodrug salts of a compound of formula I. The term "compound" also includes any solvates, hydrates, and polymorphs of any of the foregoing. The specific recitation of "prodrug," "prodrug salt," "solvate," "hydrate," or "polymorph" described herein shall not be interpreted as an intended omission of these forms where the term "compound" is used without recitation of these other forms.

A salt of a compound of formula (I) is formed between an acid and a basic group of the compound, such as an amino functional group, or a base and an acidic group of the compound, such as a carboxyl functional group. In other preferred embodiments, the compound is a pharmaceutically acceptable acid addition salt.

As used herein and unless otherwise indicated, the term "prodrug" means a derivative of a compound that can hydrolyze, oxidize, or otherwise react under biological conditions (in vitro or in vivo) to provide a disclosed compound of formula (I). Prodrugs may only become active upon such reaction under biological conditions, or they may have activity in their unreacted forms. Examples of prodrugs contemplated in the present disclosure include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, or biohydrolyzable phosphate analogues. Other examples of prodrugs include derivatives of compounds of any one of the formulae disclosed herein that comprise —NO, —$NO_2$, —ONO, or —$ONO_2$ moieties. Prodrugs may typically be prepared using well-known methods, such as those described in *Burger's Medicinal Chemistry and Drug Discovery*, Wolff, M. E., Ed. 5th ed, 1995, 172-78, 949-82. See also "Biotransformation of Drugs," *Goodman and Gilman's The Pharmacological Basis of Therapeutics*, 8th ed., 1992, McGraw-Hill, Int. Ed.

As used herein and unless otherwise indicated, the terms "biohydrolyzable amide," "biohydrolyzable ester," "biohydrolyzable carbamate," "biohydrolyzable carbonate," "biohydrolyzable ureide," and "biohydrolyzable phosphate analogue" mean an amide, ester, carbamate, carbonate, ureide, or phosphate analogue, respectively, that either (1) does not destroy the biological activity of the compound and confers upon that compound advantageous properties in vivo, such as uptake, duration of action, or onset of action; or (2) is itself biologically inactive but is converted in vivo to a biologically active compound. Examples of biohydrolyzable amides include but are not limited to lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines.

A prodrug salt is a compound formed between an acid and a basic group of the prodrug, such as an amino functional group, or a base and an acidic group of the prodrug, such as a carboxyl functional group. In some preferred embodiments, the prodrug salt is a pharmaceutically acceptable salt. In some other preferred embodiments, the counterion to the saltable prodrug of the compound of formula I is pharmaceutically acceptable. Pharmaceutically acceptable counterions include but are not limited to acids and bases noted herein as being suitable to form pharmaceutically acceptable salts. Particularly favored prodrugs and prodrug salts are ones that increase the bioavailability of the disclosed compounds of formula (I) when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group that enhances aqueous solubility or active transport through the gut membrane is appended to the structure of formulae described herein. See, e.g., Alexander, J. et al. *J. Med. Chem.* 1988, 31, 318-322; Bundgaard, H. *Design of Prodrugs,* 1985, Elsevier: Amsterdam, 1-92; Bundgaard, H. et al. *J. Med. Chem.* 1987, 30, 451-454; Bundgaard, H. *A Textbook of Drug Design and Development,* 1991, Harwood Academic Publ.: Switzerland, 113-191; Digenis, G. A. et al. *Handbook of Experimental Pharmacology,* 1975, 28, 86-112; Friis, G. J. et al. *A Textbook of Drug Design and Development,* 2nd ed., 1996, Overseas Publ.: Amsterdam, 351-385; Pitman, I. H. *Med. Res. Rev.* 1981, 1, 189-214.

As used herein, the term "pharmaceutically acceptable" refers to a component that is, within the scope of sound medical judgment, suitable for use in contact with the tissues of humans and other mammals without undue toxicity, irritation, allergic response, or other analogous negative interactions, and are commensurate with a reasonable risk/benefit ratio. A "pharmaceutically acceptable salt" means any non-toxic salt that, upon administration to a recipient, is capable of providing, either directly or indirectly, a compound or a prodrug of the disclosed compounds of formula (I). A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid, and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethane sulfonic acid, benzenesulfonic acid, lactic acid, oxalic acid, para-bromophenylsulfonic acid, carbonic acid, succinic acid, citric acid, benzoic acid, and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenyl acetate, phenylpropionate, phenylbutyrate, citrate, lactate, beta.-hydroxybutyrate, glycolate, maleate, tartrate, methanesulfonate, propanesulfonate, naphthalene-1-sulfonate, naphthalene-2-sulfonate, mandelate, and other related or analogous salts. Preferred pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or another solvent that is bound by non-covalent intermolecular forces.

As used herein, the term "polymorph" means solid crystalline forms of a compound or complex thereof which may be characterized by physical means such as, for example, X-ray powder diffraction patterns or infrared spectroscopy. Different polymorphs of the same compound may exhibit different physical, chemical, or spectroscopic properties.

Different physical properties include but are not limited to stability (e.g., heat, light, or moisture stability), compressibility and density (which may be important in formulation and product manufacturing), hygroscopicity, solubility (which may affect bioavailability), and dissolution rates. Differences in stability may result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to a thermodynamically more stable polymorph) or both (e.g., tablets of one polymorph are more susceptible to breakdown at high humidity). Different physical properties of polymorphs can affect their processing. For example, one polymorph may be more likely to form solvates or may be more difficult to filter or wash free of impurities than another polymorph due to, for example, the shape or size distribution of particles of the former.

The disclosed niraparib isotopologues are PARP inhibitors and possess unique biopharmaceutical and metabolic properties as compared to niraparib. The disclosed compounds may also be used to accurately determine the concentration of niraparib in biological fluids and to determine metabolic patterns of niraparib and its isotopologues. Compositions comprising the disclosed compounds and methods for treating BRCA-mutation positive ovarian cancer and BRCA-positive breast cancer, alone or in combination with additional agents, are also disclosed herein.

Without being bound by any theory of operation, it is believed that niraparib may be primarily metabolized by CYP3A and other drug metabolizing enzymes. The primary metabolic pathways for niraparib may involve oxidation, presumably at the benzylic carbon and/or at the electron rich nitrogen and/or α-carbons of the piperidine ring, including N-oxidation, oxidative N-dealkylation, ring oxidation, and ring opening. A radiolabeled disposition study with [$^{14}$C]-niraparib dosed IV to bile duct cannulated rats has found numerous metabolites, along with 45% of recovered radioactivity as the parent drug. See Jones, P. et al. "Niraparib: A Poly(ADP-ribose) Polymerase (PARP) Inhibitor for the Treatment of Tumors with Defective Homologous Recombination," *J. Med. Chem.* 2015, 58, 3302-3314.

Limiting the production of these metabolites has the potential to decrease the danger of the administration of niraparib and related drugs and may even allow increased dosage and concomitant increased efficacy. All of these transformations may occur through polymorphically-expressed enzymes, thus exacerbating the interpatient variability. For all of the foregoing reasons, there is a strong likelihood that a drug with a longer half-life will diminish the aforementioned problems and result in greater efficacy and cost savings.

Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, and/or (f) decrease the production of deleterious metabolites in specific tissues and/or create a more effective drug and/or a safer drug for both intentional and unintentional polypharmacy. Deuteration offers a strong potential to slow drug metabolism via various oxidative and other modification mechanisms. In particular, deuteration of drugs produces benefits when using combinations of different medications, which is common for patients suffering from cancer.

The disclosed compounds and compositions are also useful as analytical reagents for determining the concentration of niraparib in solution. As used herein, niraparib refers to the compound wherein all hydrogen atoms and all carbon atoms are present at the approximate percentages of their natural isotopic abundance. While some variation of natural isotopic abundance does occur depending upon the origin of chemical starting materials and reagents, the concentration of naturally abundant stable hydrogen and carbon isotopes, notwithstanding this variation, is small and immaterial with respect to the degree of stable isotopic substitution of compounds disclosed herein. See, e.g., Wada, E. et al. *Seikagaku,* 1994 66, 15; Ganes, L. Z. et al. *Comp. Biochem. Physiol. A Mol. Integr. Physiol.* 1998, 119, 725.

The altered properties of the disclosed compounds will not significantly affect their ability to bind to their protein target. This is because such binding is primarily dependent upon non-covalent binding between the protein and the inhibitor, and may be impacted both positively and negatively by isotopic substitution depending on the specific substitution involved, and any negative effects that a heavier atom in the disclosed compounds may have on the highly optimized non-covalent binding between the disclosed compounds and their targeted proteins will be relatively minor. Major factors contributing to the noncovalent recognition of small molecules by proteins and the binding strength between them include Van der Waals forces, hydrogen bonds, ionic bonds, molecular reorganization, desolvation energy of the small molecule, hydrophobic interactions, and, in some situations, displacement energy for pre-existing bound ligands. See, e.g., *Goodman & Gilman's The Pharmacological Basis of Therapeutics, Tenth Edition,* Hardman, J. G. et al., Eds. 2001, McGraw-Hill; *The Organic Chemistry of Drug Design and Drug Action,* Silverman, R. B., 2004, Academic Press.

The disclosed compounds possess molecular topologies very similar to niraparib, as the exchange of deuterium for hydrogen does not appreciably alter molecular configuration, and the exchange of $^{13}$C for $^{12}$C is conformationally neutral. See Holtzer, M. E. et al. *Biophys. J.* 2001, 80, 939. Deuterium replacement does cause a slight decrease in Van der Waals radius, see Wade, D. *Chem. Biol. Interact.* 1999, 117, 191, but such decrease will likely not appreciably reduce the binding affinity between the disclosed compounds and their receptors as compared to niraparib. Further, the slightly smaller size of the disclosed deuterated compounds prevents additional undesirable steric interactions with the binding protein as compared to niraparib.

Neither deuterium nor $^{13}$C atoms in the disclosed compounds contribute significantly to hydrogen bonding or ionic interactions with the protein receptors. This is because the major hydrogen bond and ionic interactions formed by niraparib with its targeted proteins are mediated by the oxygens, nitrogens, and the amine-bound hydrogens within niraparib. Any deuterium atoms attached to the amine nitrogen will be rapidly exchanged with bulk solvent protons under physiological conditions. Protein reorganization or side chain movement will be identical between the disclosed compounds and niraparib. Desolvation energy of the disclosed compounds will be equivalent to or less than that of niraparib, resulting in neutral or increased binding affinity for the receptor. See Turowski, M. et al. *J. Am. Chem. Soc.* 2003, 125, 13836. The replacement of $^{12}$C by $^{13}$C in the disclosed compounds will also cause no significant change in desolvation energy. Thus, the disclosed compounds will advantageously retain substantial PARP inhibitory activity with a reduced rate of metabolite generation.

The disclosed compounds and compositions are also useful as analytical reagents for determining the concentration of niraparib in solution.

In some preferred embodiments, the deuterated compounds disclosed herein maintain the beneficial properties of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

In some preferred embodiments, $Y^9$, $Y^{9'}$, $Y^{10}$, and $Y^{10'}$ of the compounds of formula (I) are each deuterium, and $Y^1$, $Y^2$, $Y^3$, $Y^4$, $Y^5$, $Y^6$, $Y^7$, $Y^8$, $Y^{11}$, $Y^{11'}$, $Y^{12}$, $Y^{12'}$, and $Y^{13}$ are each hydrogen.

In some preferred embodiments, $Y^9$, $Y^{9'}$, $Y^{10}$, $Y^{10'}$, $Y^{11}$, $Y^{11'}$, $Y^{12}$, $Y^{12'}$, and $Y^{13}$ of the compounds of formula (I) are each deuterium, and $Y^1$, $Y^2$, $Y^3$, $Y^4$, $Y^5$, $Y^6$, $Y^7$, and $Y^8$ are each hydrogen.

In some preferred embodiments, $Y^9$, $Y^{10}$, $Y^{11}$, and $Y^{12}$ of the compounds of formula (I) are each deuterium, and $Y^1$, $Y^2$, $Y^3$, $Y^4$, $Y^5$, $Y^6$, $Y^7$, $Y^8$, $Y^{9'}$, $Y^{10'}$, $Y^{11'}$, $Y^{12'}$, and $Y^{13}$ are each hydrogen.

In some preferred embodiments, $Y^9$, $Y^{10}$, $Y^{11}$, $Y^{12}$, and $Y^{13}$ of the compounds of formula (I) are each deuterium, and $Y^1$, $Y^2$, $Y^3$, $Y^4$, $Y^5$, $Y^6$, $Y^7$, $Y^8$, $Y^{9'}$, $Y^{10'}$, $Y^{11'}$, and $Y^{12'}$ are each hydrogen.

In some preferred embodiments, $Y^9$ and $Y^{13}$ of the compounds of formula (I) are each deuterium, and $Y^1$, $Y^2$, $Y^3$, $Y^4$, $Y^5$, $Y^6$, $Y^7$, $Y^8$, $Y^{9'}$, $Y^{10}$, $Y^{10'}$, $Y^{11}$, $Y^{11'}$, $Y^{12}$, and $Y^{12'}$ are each hydrogen.

In some preferred embodiments, $Y^4$ of the compounds of formula (I) is a deuterium, and $Y^1$, $Y^2$, $Y^3$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ are each hydrogen.

In some preferred embodiments, $Y^5$, $Y^6$, $Y^7$, and $Y^8$ of the compounds of formula (I) are each deuterium, and $Y^1$, $Y^2$, $Y^3$, $Y^4$, $Y^9$, $Y^{9'}$, $Y^{10}$, $Y^{10'}$, $Y^{11}$, $Y^{11'}$, $Y^{12}$, $Y^{12'}$, and $Y^{13}$ are each hydrogen.

In some preferred embodiments, $Y^5$, $Y^6$, $Y^7$, $Y^8$, $Y^9$, and $Y^{13}$ of the compounds of formula (I) are each deuterium, and $Y^1$, $Y^2$, $Y^3$, $Y^4$, $Y^{9'}$, $Y^{10}$, $Y^{10'}$, $Y^{11}$, $Y^{11'}$, $Y^{12}$, and $Y^{12'}$ are each hydrogen.

In some preferred embodiments, $Y^5$, $Y^6$, $Y^7$, $Y^8$, $Y^9$, $Y^{10}$, $Y^{11}$, and $Y^{12}$ of the compounds of formula (I) are each deuterium, and $Y^1$, $Y^2$, $Y^3$, $Y^4$, $Y^{9'}$, $Y^{10'}$, $Y^{11'}$, $Y^{12'}$, and $Y^{13}$ are each hydrogen.

In some preferred embodiments, $Y^5$, $Y^6$, $Y^7$, $Y^8$, $Y^9$, $Y^{10}$, $Y^{11}$, $Y^{12}$, and $Y^{13}$ of the compounds of formula (I) are each deuterium, and $Y^1$, $Y^2$, $Y^3$, $Y^4$, $Y^{9'}$, $Y^{10'}$, $Y^{11'}$, and $Y^{12'}$ are each hydrogen.

In some preferred embodiments, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ of the compounds of formula (I) are each deuterium, and $Y^1$, $Y^2$, $Y^3$, and $Y^4$ are each hydrogen.

In some preferred embodiments, $Y^4$, $Y^5$, $Y^6$, $Y^7$, and $Y^8$ of the compounds of formula (I) are each deuterium, and $Y^1$, $Y^2$, $Y^3$, $Y^9$, $Y^{9'}$, $Y^{10}$, $Y^{10'}$, $Y^{11}$, $Y^{11'}$, $Y^{12}$, $Y^{12'}$, and $Y^{13}$ are each hydrogen.

In some preferred embodiments, $Y^4$, $Y^9$, $Y^{9'}$, $Y^{10}$, $Y^{10'}$, $Y^{11}$, $Y^{11'}$, $Y^{12}$, $Y^{12'}$, and $Y^{13}$ of the compounds of formula (I) are each deuterium, and $Y^1$, $Y^2$, $Y^3$, $Y^5$, $Y^6$, $Y^7$, and $Y^8$ are each hydrogen.

In some preferred embodiments, $Y^4$, $Y^9$, $Y^{10}$, $Y^{11}$, and $Y^{12}$ of the compounds of formula (I) are each deuterium, and $Y^1$, $Y^2$, $Y^3$, $Y^5$, $Y^6$, $Y^7$, $Y^8$, $Y^{9'}$, $Y^{10'}$, $Y^{11'}$, $Y^{12'}$, and $Y^{13}$ are each hydrogen.

In some preferred embodiments, $Y^4$, $Y^9$, $Y^{10}$, $Y^{11}$, $Y^{12}$, and $Y^{13}$ of the compounds of formula (I) are each deuterium, and $Y^1$, $Y^2$, $Y^3$, $Y^5$, $Y^6$, $Y^7$, $Y^8$, $Y^9$', $Y^{10'}$, $Y^{11'}$, and $Y^{12'}$ are each hydrogen.

In some preferred embodiments, $Y^4$ and $Y^{13}$ of the compounds of formula (I) are each deuterium, and $Y^1$, $Y^2$, $Y^3$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, and $Y^{12'}$ are each hydrogen.

In some preferred embodiments, $Y^4$, $Y^9$, and $Y^{13}$ of the compounds of formula (I) are each deuterium, and $Y^1$, $Y^2$, $Y^3$, $Y^5$, $Y^6$, $Y^7$, $Y^8$, $Y^{9'}$, $Y^{10}$, $Y^{10'}$, $Y^{11}$, $Y^{11'}$, $Y^{12}$, and $Y^{12'}$ are each hydrogen.

In some preferred embodiments, $Y^{13}$ of the compounds of formula (I) is a deuterium, and $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, and $Y^{12'}$ are each hydrogen.

In some preferred embodiments, $Y^9$, $Y^{9'}$, $Y^{12}$, and $Y^{12'}$ of the compounds of formula (I) are each deuterium, and $Y^1$, $Y^2$, $Y^3$, $Y^4$, $Y^5$, $Y^6$, $Y^7$, $Y^8$, $Y^{10}$, $Y^{10'}$, $Y^{11}$, $Y^{11'}$, and $Y^{13}$ are each hydrogen.

In some preferred embodiments, $Y^2$ of the compounds of formula (I) is a deuterium, and $Y^1$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ are each hydrogen.

In some preferred embodiments, $Y^5$, $Y^6$, $Y^7$, $Y^8$, $Y^9$, $Y^{9'}$, $Y^{10}$, and $Y^{10'}$ of the compounds of formula (I) are each deuterium, and $Y^1$, $Y^2$, $Y^3$, $Y^4$, $Y^{11}$, $Y^{11'}$, $Y^{12}$, $Y^{12'}$, and $Y^{13}$ are each hydrogen.

In some preferred embodiments, $Y^2$, $Y^9$, $Y^{9'}$, $Y^{10}$, and $Y^{10'}$ of the compounds of formula (I) are each deuterium, and $Y^1$, $Y^3$, $Y^4$, $Y^5$, $Y^6$, $Y^7$, $Y^8$, $Y^{11}$, $Y^{11'}$, $Y^{12}$, $Y^{12'}$, and $Y^{13}$ are each hydrogen.

In some preferred embodiments, $Y^2$, $Y^5$, $Y^6$, $Y^7$, $Y^8$, $Y^9$, $Y^{9'}$, $Y^{10}$, and $Y^{10'}$ of the compounds of formula (I) are each deuterium, and $Y^1$, $Y^3$, $Y^4$, $Y^{11}$, $Y^{11'}$, $Y^{12}$, $Y^{12'}$, and $Y^{13}$ are each hydrogen.

In some preferred embodiments, $Y^5$, $Y^6$, $Y^7$, $Y^8$, $Y^9$, $Y^{9'}$, $Y^{12}$, and $Y^{12'}$ of the compounds of formula (I) are each deuterium, and $Y^1$, $Y^2$, $Y^3$, $Y^4$, $Y^{10}$, $Y^{10'}$, $Y^{11}$, $Y^{11'}$, and $Y^{13}$ are each hydrogen.

In some preferred embodiments, $Y^2$, $Y^9$, $Y^{9'}$, $Y^{12}$, and $Y^{12'}$ of the compounds of formula (I) are each deuterium, and $Y^1$, $Y^3$, $Y^4$, $Y^5$, $Y^6$, $Y^7$, $Y^8$, $Y^{10}$, $Y^{10'}$, $Y^{11}$, $Y^{11'}$, and $Y^{13}$ are each hydrogen.

In some preferred embodiments, $Y^2$, $Y^5$, $Y^6$, $Y^7$, $Y^8$, $Y^9$, $Y^{9'}$, $Y^{12}$, and $Y^{12'}$ of the compounds of formula (I) are each deuterium, and $Y^1$, $Y^3$, $Y^4$, $Y^{10}$, $Y^{10'}$, $Y^{11}$, $Y^{11'}$, and $Y^{13}$ are each hydrogen.

In some preferred embodiments, $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ of the compounds of formula (I) are each deuterium.

The following abbreviations are used herein:

Abbreviations

Ac acetyl
ACN acetonitrile
AcOH or HOAc acetic acid
aq. aqueous anhyd. anhydrous
ATP adenosine triphosphate
Bn benzyl
Bu butyl
Boc or BOC tert-butoxycarbonyl
BOP benzotriazole-1-yl-oxy-tris-(dimethylamino)-phosphonium hexafluorophosphate
CDI carbonyldiimidazole
° C. degrees Celcius
Cbz carbobenzyloxy
Conc. concentration
d days
DAST (diethylamino)sulfur trifluoride
DBU 1,8-diazabicyclo[5.4.0]undec-7-ene
DCE 1,2-dichloroethane
DCM dichloromethane
DEA diethylamine
DIEA or DIPEA diisopropylethylamine
DMAP dimethylaminopyridine
DMA N,N-dimethylacetamide
DME 1,2-dimethoxyethane
DMF dimethylformamide
DMSO dimethylsulfoxide
DPPA diphenylphosphorylazide
dppf 1,1'-bis(diphenylphosphino)ferrocene
DTT dithiothreitol
EDC or EDCI or EDAC 1-(3-dimethyl aminopropyl)-3-ethyl carb odiimi de hydrochloride
EDTA ethylenediaminetetraacetic acid
ee enantiomeric excess
EGTA ethylene glycol tetraacetic acid
eq. or Eq. or equiv. equivalents
EtOAc or EA ethyl acetate
Et ethyl
EtOH ethanol
Ex example
GST glutathione S-transferase
HATU N,N,N,N-tetramethyl-O-(7-azabenzotriazol-1-yl) uronium hexafluorophosphate
Hex hexanes
HIS histidine
h or hr hours
i iso
IPA isopropanol
Hz hertz
MHz megahertz
HPLC high pressure liquid chromatography
RP-HPLC reverse-phase high pressure liquid chromatography
HOBT 1-hydroxybenzotriazole hydrate
Lawesson's Reagent [2,4-bis(4-methoxyphenyl)-1,3-dithia-2,4-diphosphetane-2-4-disulfide
LC liquid chromatography
LCMS or LC/MS liquid chromatograph mass spectrometry
LDA lithium diisopropylamide
m-CPBA or MCPBA meta-chloroperbenzoic acid
Me methyl
MeOH methanol
min. minutes
$M^+$ $(M+H)^+$
$M^{+1}$ $(M+H)^+$
MS mass spectrometry
MSA methanesulfonic acid
MTBE methyl tert-butyl ether
m/z mass to charge ratio
N Normal
NMP N-methylpyrrolidinone
NMR nuclear magnetic resonance
PBMC peripheral blood mononuclear cells
PhCONCS benzyolyisothiocyanate
Pd/C palladium on carbon
Ph phenyl
Pr propyl
PHA phytohemagglutinin
ppm parts per million
PSI or psi pounds per square inch
quant. quantitative
Ret Time or Rt retention time
rt or RT room temperature
sat. or sat'd. saturated
sec seconds
S-Tol-BINAP (S)-(−)-2,2'-bis(di-p-tolylphosphino)-1,1'-binapthyl
SM or sm starting material
t tert
TEA triethylamine
TFA trifluoroacetic acid
THF tetrahydrofuran
TLC thin layer chromatography
TMS-I or TMSI iodotrimethylsilane
p-TSA para-toluenesulfonic acid
W/V or w/v weight to volume
Xantphos® (9,9-dimethyl-9H-xanthene-4,5-diyl)bis[diphenylphosphine]
X-Phos dicyclohexyl(2',4',6'-triisopropylbiphenyl-2-yl) phosphine
t triplet
m multiplet
s singlet
d doublet
br. s. broad singlet
dd doublet of doublets
tt triplet of triplets
ddd doublet of doublet of doublets
q quartet
quin. quintet The following examples are provided as specific illustrations. It should be understood, however, that the invention is not limited to the specific details set forth in the examples. All parts and percentages in the examples, as well as in the remainder of the disclosure, are by weight unless otherwise specified.

Further, any range of numbers recited above or in the paragraphs hereinafter describing or claiming various aspects of the invention, such as ranges that represent a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for or in conjunction with a variable, is intended to convey that the numbers and ranges disclosed herein may be flexible as understood by ordinarily skilled artisans and that practice of the disclosed invention by those skilled in the art using temperatures, concentrations, amounts, contents, carbon numbers, and properties that are outside of a literal range will achieve the desired result, namely, using the disclosed compounds of formula (I) as PARP inhibitors in the treatment of patients with BRCA-mutation positive ovarian cancer and BRCA-positive breast cancer.

Preparation of Compounds

Example 1

Methods of Preparation and Analysis

The compounds of formula (I) may be prepared by the processes described herein in reaction Scheme A. Examples of suitable reagents and procedures for conducting these reactions appear hereinafter and in the working examples included therein. Protection and deprotection in the schemes herein may be carried out by procedures generally known in the art. See, e.g., Greene, T. W. et al. *Protecting Groups in Organic Synthesis*, 4th Ed., 2007, Wiley.

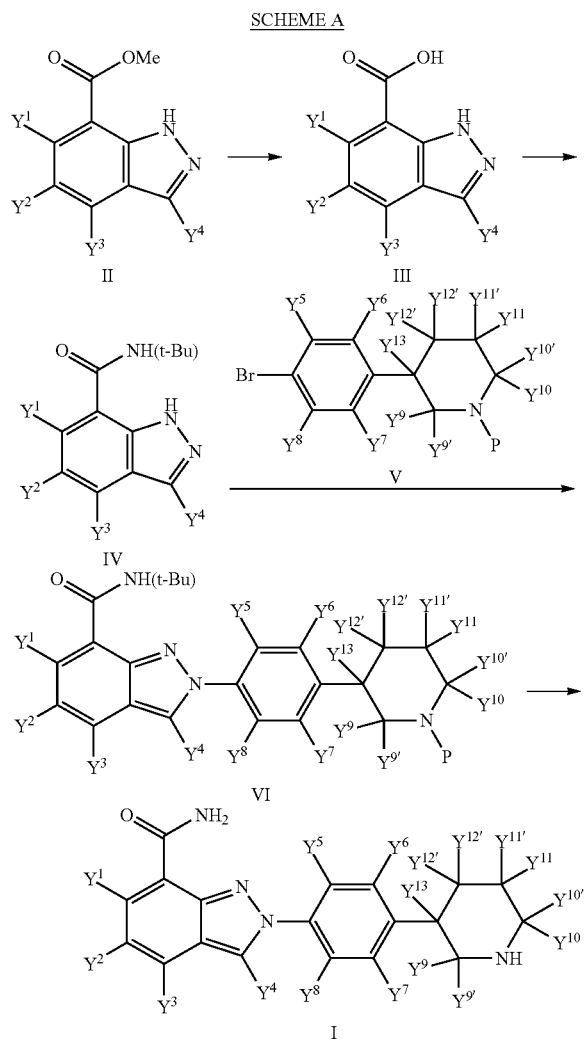

SCHEME A

Compounds of formula (I) may be prepared from compounds of formula (II) as depicted in Scheme A. See *Org. Process Res. Dev.* 2014, 18, 215-227.

Conversion of compounds of formula (II) to compounds of formula (IV) may be achieved via hydrolysis and amination reactions using the procedures known to chemists with the state-of-the-art knowledge.

Reaction of compounds of formula (IV) and compounds of formula (V), wherein P is an N-protecting group and preferably a BOC group, are conducted according to the procedures similar to those described in the reference literature, see *Org. Process Res. Dev.* 2014, 18, 215-227 and references cited therein, to form compounds of formula (VI) via a regioselective CN coupling reaction. The reaction may be carried out in an organic solvent, preferably DMA, in the presence of a copper (I) catalyst such as CuBr and a base such as $K_2CO_3$ at an elevated temperature, preferably at about 110° C.

Removal of the BOC protecting group under acidic conditions may yield compounds of formula (I).

Alternatively, compounds of formula (I) may be prepared from compounds of formulas (VII) and (VIII) as depicted in reaction Scheme B.

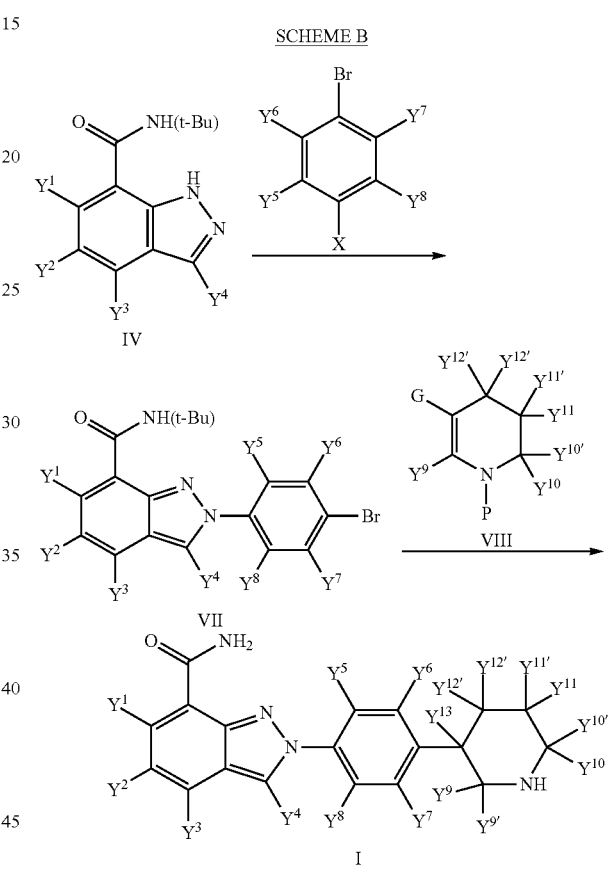

SCHEME B

Conversion of compounds of formula (IV) to compounds of formula (VII) may be achieved via copper-catalyzed C—N coupling reactions using the procedures known to chemists with the state-of-the-art knowledge.

Reaction of compounds of formula (VII) and compound of formula (VIII), wherein P is an N-protecting group and preferably a BOC group, and wherein G is a coupling group and preferably a boronic acid or ester group, or a metal-containing group, are conducted via procedures similar to those described in the reference literature, see *Org. Process Res. Dev.* 2014, 18, 215-227 and references cited therein, to form the coupling product, followed by hydrogenation and removal of the BOC protecting group under the acidic conditions to generate compounds of formula (I).

Analytical LCMS Conditions:

Method A: HPLC: Shimadzu LC-2010/LCMS: ThermoFisher LTQ XL. Column: Hypersil Gold 2.1×50 mm 3 µm; mobile phase: 3% solvent B/A for 0.5 min, gradient 3-95% B/A in 5 min with 0.2 min hold at 95% B/A, gradient 95-3% B/A in 0.01 min with 2.5 min hold at 3% B/A; flow rate: 0.4 mL/min; Solvent A: 5/95 MeOH/water with 0.1% formic acid; Solvent B: 5/95 MeOH/acetonitrile with 0.1% formic acid; products detected at 220 or 254 nM wavelength with positive ionization mode.

Analytical GCMS Conditions:

Method B: Shimadzu GC-2010/GCMS-QP2010S. Primary column: SLB-5 ms 30 m×0.25 mm, 0.25 µm; GC oven temperature program total 15 min, 45° C. to 300° C. at 40° C./min with 10 min hold at 300° C.; carrier gas He; inlet pressure 50 kPa; column flow rate 1.0 ml/min. Product detected by electron ionization mode.

Example 2

2-(4-(piperidin-3-yl-2,2,3,4,4,5,5,6,6-d$_9$)phenyl-2,3, 5,6-d$_4$)-2H-indazole-7-carboxamide

Step 1: tert-butyl 3-(4-(7-(tert-butylcarbamoyl)-2H-indazol-2-yl)phenyl-2,3,5,6-d$_4$)piperidine-1-carboxylate-2,2,3,4,4,5,5,6,6-d$_9$

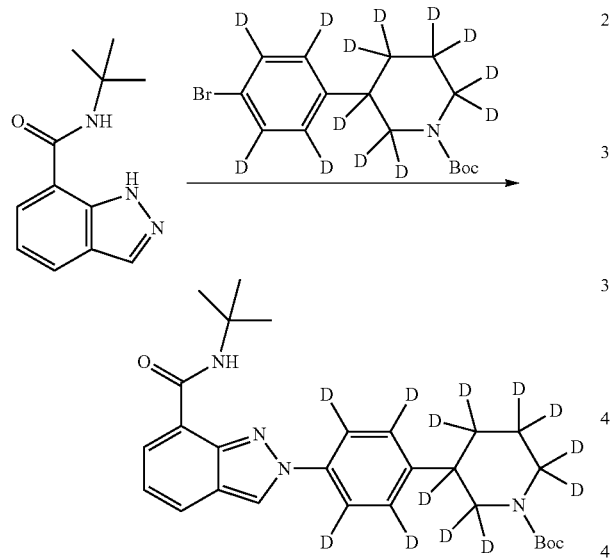

To a solution of tert-butyl 3-(4-bromophenyl-2,3,5,6-d$_4$)piperidine-1-carboxylate-2,2,3,4,4,5,5,6,6-d$_9$ (200 mg, 0.566 mmol, commercially available) in 4 mL of DMAc were added N-(tert-butyl)-1H-indazole-7-carboxamide (130 mg, 0.598 mmol), prepared from methyl 1H-indazole-7-carboxylate according to the literature procedure, see Chung, C. K. et al. *Org. Process Res. Dev.* 2014, 18, 215-27, and K$_2$CO$_3$ (250 mg, 1.81 mmol) at room temperature. The mixture was degassed with N$_2$ over a period of 5 min. CuBr (10 mg, 0.0696 mmol) and 8-hydroxyquinoline (20 mg, 0.138 mmol) were added, and N$_2$ purging continued for 10 min. The mixture was then heated to 110° C. for 24 h. After cooling to 40° C., Celite was added, and the mixture was stirred for 1 h before being filtered, washing the cake with DMAc (1×10 mL). The combined filtrates were adjusted to 35° C., and then DMAc (5 mL) and 10% aq. citric acid (1 mL) were added. The resulting slurry was allowed to stand for 2 h at 35° C. then at 20-25° C. overnight. Filtration, washing with 2:1 v/v DMAc/water (1×10 mL) followed by water (1×3 mL), and drying in vacuo yielded 135 mg of tert-butyl 3-(4-(7-(tert-butylcarbamoyl)-2H-indazol-2-yl) phenyl-2,3,5,6-d$_4$)piperidine-1-carboxylate-2,2,3,4,4,5,5,6, 6-d$_9$ (49% yield) as a light yellow powder.

Alternative purification method: The product mixture was partitioned in water and dichloromethane. After separation, the organic layer was washed with brine, dried and concentrated. The resulting residue was purified by flash column (Combiflash RF+, DCM to 85% DCM/10% MeOH/5% NH$_4$OH) to afford tert-butyl 3-(4-(7-(tert-butylcarbamoyl)-2H-indazol-2-yl)phenyl-2,3,5,6-d$_4$)piperidine-1-carboxylate-2,2,3,4,4,5,5,6,6-d$_9$ as a light yellow powder.

Step 2: 2-(4-(piperidin-3-yl-2,2,3,4,4,5,5,6,6-d$_9$) phenyl-2,3,5,6-d$_4$)-2H-indazole-7-carboxamide

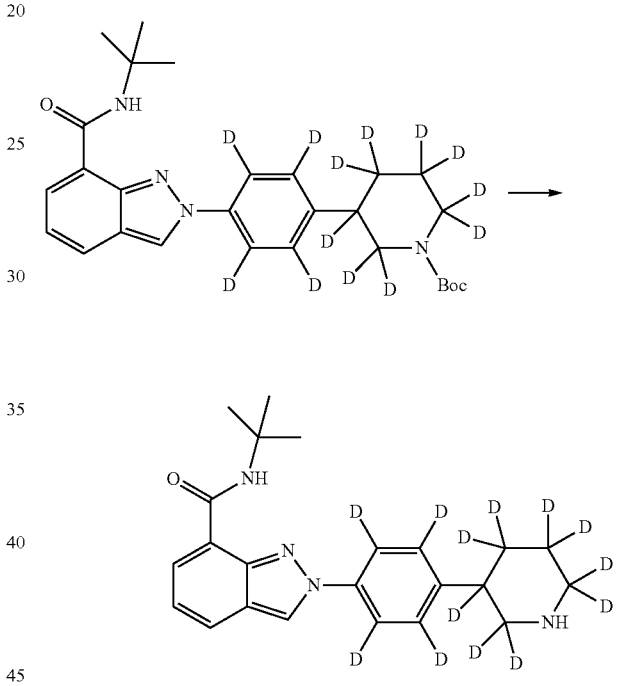

To a stirred solution of tert-butyl 3-{4-[7-(aminocarbonyl)-2H-indazol-2-yl]phenyl}piperidine-1-carboxylate (135 mg, 0.276 mmol) in xylene (1.0 mL) was added CH$_3$SO$_3$H (1.5 mL), and the reaction mixture was stirred at 40° C. for 2.5 h followed by addition of H$_2$O (3.5 mL) and K$_2$CO$_3$ at 0° C. The solvent was evaporated under reduced pressure and the crude product purified by trituration with Et$_2$O to yield the desired product (35 mg, 38%) as a yellow solid. $^1$H NMR (300 MHz, DMSO-d$_6$): δ 9.31 (s, 1H), 8.58 (s, 1H), 8.05-7.95 (m, 3H), 7.27 (br. 1H). LCMS (Method A): m/z 334.3 ([M+H]$^+$), HPLC Rt 0.85 min.

Alternative purification method: The layers were then separated, and the aqueous layer was washed with ethyl ether, filtered, and adjusted to above pH 7. The product mixture was partitioned in water and dichloromethane. After separation, the organic layer was washed with brine, dried, and concentrated. The resulting residue was purified by flash column (Combiflash RF+, DCM to 85% DCM/10% MeOH/ 5% NH$_4$OH) to afford afforded the title compound of Example 2 as a white powder (35 mg, 38% yield).

Example 3

2-(4-(piperidin-3-yl-2,2,3,4,4,5,5,6,6-d$_9$)phenyl)-2H-indazole-7-carboxamide

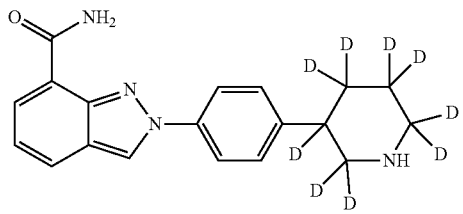

According to the procedures described for Example 2, Example 3 was prepared from N-(tert-butyl)-1H-indazole-7-carboxamide (380 mg, 1.75 mmol) and tert-butyl 3-(4-bromophenyl)piperidine-1-carboxylate-2,2,3,4,4,5,5,6,6-d$_9$ (600 mg, 1.72 mmol, commercially available) under conditions similar to Steps 1 and 2 in Example 2 to afford 230 mg (40% yield) of the title product. $^1$H NMR (300 MHz, DMSO-d$_6$): δ 9.28 (s, 1H), 8.58 (s, 1H), 8.07-8.01 (m, 4H), 7.89 (s, 1H), 7.48 (d, J=8.4 Hz, 2H), 7.27 (dd, J=7.5 Hz, 7.8 Hz, 1H). LCMS (Method A): m/z 330.2 ([M+H]$^+$), HPLC Rt 6.98 min.

Example 4

2-(4-(piperidin-3-yl-2,3,4,5,6-d$_5$)phenyl-2,3,5,6-d$_4$)-2H-indazole-7-carboxamide

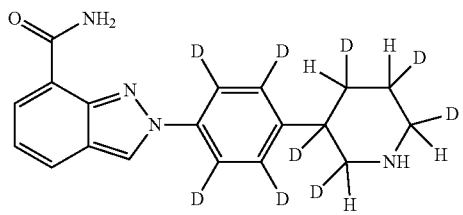

According to the procedures described for Example 2, Example 4 was prepared from N-(tert-butyl)-1H-indazole-7-carboxamide (1.3 g, 5.99 mmol) and tert-butyl 3-(4-bromophenyl-2,3,5,6-d$_4$)piperidine-1-carboxylate-2,3,4,5,6-d$_5$ (2.0 g, 5.73 mmol, commercially available) under conditions similar to Steps 1 and 2 in Example 2 to afford 0.51 g (27% yield) of the title product. $^1$H NMR (300 MHz, DMSO-d$_6$): δ 9.28 (s, 1H), 8.58 (s, 1H), 8.08-8.01 (m, 2H), 7.90 (s, 1H), 7.27 (dd, J=7.5 Hz, 7.8 Hz, 1H), 3.08-2.95 (m, 1H), 2.64 (m, 1H), 1.68-1.60 (m, 2H). LCMS (Method A): m/z 330.3 ([M+H]$^+$), HPLC Rt 6.93 min.

Example 5

2-(4-(piperidin-3-yl-2,3,4,5,6-d$_5$)phenyl)-2H-indazole-7-carboxamide

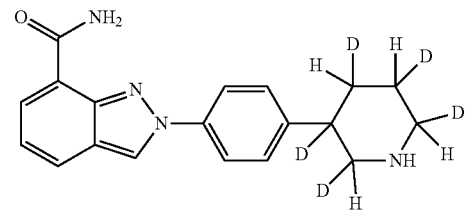 [SMILES: [2H]C1([2H])NC([2H])([2H])C([2H])(c2ccc(-n3cc4cccc(C(N)=O)c4n3)cc2)C([2H])([2H])C1([2H])[2H]]

According to the procedures described for Example 2, Example 5 was prepared from N-(tert-butyl)-1H-indazole-7-carboxamide (1.32 g, 6.1 mmol) and tert-butyl 3-(4-bromophenyl)piperidine-1-carboxylate-2,3,4,5,6-d$_5$ (2.1 g, 6.1 mmol, commercially available) under conditions similar to Steps 1 and 2 in Example 2 to afford 35 g (18% yield) of the title product. $^1$H NMR (300 MHz, DMSO-d$_6$): δ 9.29 (s, 1H), 8.58 (s, 1H), 8.09-8.01 (m, 4H), 7.90 (s, 1H), 7.49 (d, J=8.4 Hz, 2H), 7.27 (dd, J=7.5 Hz, 7.8 Hz, 1H), 3.08-2.95 (m, 1H), 2.71 (m, 1H), 1.71-1.62 (m, 2H). LCMS (Method A): m/z 326.2 ([M+H]$^+$), HPLC Rt 6.78 min.

Example 6

2-(4-(piperidin-3-yl-2,4,5,6-d$_4$)phenyl-2,3,5,6-d$_4$-2H-indazole-7-carboxamide

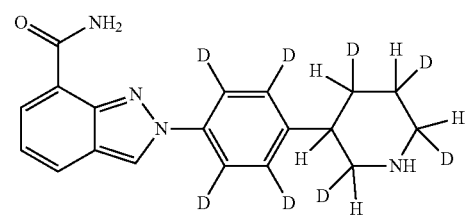 [SMILES: [2H]c1c([2H])c(C2([2H])C([2H])NC([2H])C([2H])C2[2H])c([2H])c([2H])c1-n1cc2cccc(C(N)=O)c2n1]

According to the procedures described for Example 2, Example 6 was prepared from N-(tert-butyl)-1H-indazole-7-carboxamide (300 mg, 0.86 mmol) and tert-butyl 3-(4-bromophenyl-2,3,5,6-d$_4$)piperidine-1-carboxylate-2,4,5,6-d$_4$ (190 mg, 0.88 mmol, commercially available) under conditions similar to Steps 1 and 2 in Example 2 to afford 200 mg (71% yield) of the title product. $^1$H NMR (300 MHz, DMSO-d$_6$): δ 9.28 (s, 1H), 8.58 (s, 1H), 8.07-8.01 (m, 2H), 7.89 (s, 1H), 7.28 (dd, J=7.5 Hz, 7.8 Hz, 1H), 3.07-2.94 (m, 1H), 2.76-2.66 (m, 1H), 1.96-1.89 (m, 1H), 1.65-1.56 (m, 2H). LCMS (Method A): m/z 329.2 ([M+H]$^+$), HPLC Rt 6.97 min.

Example 7

2-(4-(piperidin-3-yl-2,4,5,6-d₄)phenyl)-2H-indazole-7-carboxamide

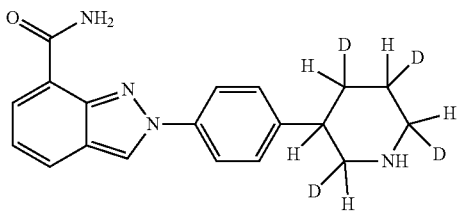 [SMILES: [2H]C1NC([2H])C(c2ccc(-n3cc4cccc(C(N)=O)c4n3)cc2)C([2H])C1[2H]]

According to the procedures described for Example 2, Example 7 was prepared from N-(tert-butyl)-1H-indazole-7-carboxamide (190 mg, 0.87 mmol) and tert-butyl 3-(4-bromophenyl)piperidine-1-carboxylate-2,4,5,6-d₄ (300 mg, 0.87 mmol, commercially available) under conditions similar to Steps 1 and 2 in Example 2 to afford 100 mg (35% yield) of the title product. $^1$H NMR (300 MHz, DMSO-d₆): δ 9.28 (s, 1H), 8.58 (s, 1H), 8.08-8.01 (m, 4H), 7.89 (s, 1H), 7.48 (d, J=8.4 Hz, 2H), 7.27 (dd, J=7.5 Hz, 7.8 Hz, 1H), 3.07-2.94 (m, 1H), 2.76-2.66 (m, 1H), 1.96-1.89 (m, 1H), 1.65-1.56 (m, 2H). LCMS (Method A): m/z 325.2 ([M+H]$^+$), HPLC Rt 6.97 min.

Example 8

2-(4-(piperidin-3-yl)phenyl-2,3,5,6-d₄)-2H-indazole-7-carboxamide

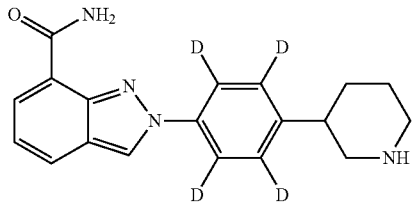 [SMILES: [2H]c1c([2H])c(-n2cc3cccc(C(N)=O)c3n2)c([2H])c([2H])c1C1CCCNC1]

Scheme A

According to the procedures described for Example 2, Example 8 was prepared from N-(tert-butyl)-1H-indazole-7-carboxamide (4.8 g, 22.1 mmol) and tert-butyl 3-(4-bromophenyl-2,3,5,6-d₄)piperidine-1-carboxylate (8.0 g, 23.2 mmol, commercially available) under conditions similar to Steps 1 and 2 in Example 2 to afford 1.15 g (16% yield) of the title product.

Scheme B

Step 1: 2-(4-bromophenyl-2,3,5,6-d₄)-N-(tert-butyl)-2H-indazole-7-carboxamide

A mixture of 1,4-dibromobenzene-2,3,5,6-d₄ (5.5 g, 22.9 mmol, commercially available), N-(tert-butyl)-1H-indazole-7-carboxamide (5.0 g, 23.0 mmol), K₂CO₃ (9.6 g, 69.5 mmol), CuBr (0.23 g, 1.6 mmol), and 8-hydroxyquinoline (0.5 g, 3.44 mmol) in DMAc (80 mL) was heated to 110° C. for 20 h. After cooling to 40° C., Celite (10 g) was added, and the mixture was stirred for 1 h before being filtered, washing the cake with DMAc (1×50 mL). After 50 mL of H₂O was added, the phases were separated and the aqueous layer was extracted twice with EtOAc (2×100 mL). The combined organic layers were washed with water (50 mL) and brine (50 mL) and dried over MgSO₄. The organic phase was concentrated under reduced pressure, and the crude product was purified by flash chromatography on silica gel using a mixture of hexane/ethyl acetate (8:1) as eluent to yield 3.8 g of 2-(4-bromophenyl-2,3,5,6-d₄)-N-(tert-butyl)-2H-indazole-7-carboxamide (44% yield) as a solid.

Step 2: tert-butyl 5-(4-(7-(tert-butylcarbamoyl)-2H-indazol-2-yl)phenyl-2,3,5,6-d₄)-3,4-dihydropyridine-1(2H)-carboxylate A mixture of 2-(4-bromophenyl-2,3,5,6-d₄)-N-(tert-butyl)-2H-indazole-7-carboxamide (3.8 g, 10.1 mmol), tert-butyl 5-(4,4,5,5-tetramethyl-1,3,2-dioxaborolan-2-yl)-3,4-dihydropyridine-1(2H)-carboxylate (3.1 g, 10.0 mmol, commercially available), [1,1'-bis (diphenylphosphino)ferrocene] dichloropalladium (II) (0.38 g, 0.46 mmol), and potassium carbonate (3.0 g, 21.7 mmol) in dioxane (30 mL) was stirred at 110° C. for 16 h. After quenching with saturated aqueous ammonium chloride solution, the mixture was partitioned between ethyl acetate and water, and the crude product from the organic phase was chromatographed on silica gel eluting with a 1:9 mixture of ethyl acetate and hexane, to yield 2.2 g (46% yield) of tert-butyl 5-(4-(7-(tert-butylcarbamoyl)-2H-indazol-2-yl)phenyl-2,3,5,6-d₄)-3,4-dihydropyridine-1(2H)-carboxylate as a solid.

Step 3: tert-butyl 3-(4-(7-(tert-butylcarbamoyl)-2H-indazol-2-yl)phenyl-2,3,5,6-d₄)piperidine-1-carboxylate A suspension of tert-butyl 5-(4-(7-(tert-butylcarbamoyl)-2H-indazol-2-yl)phenyl-2,3,5,6-d₄)-3,4-dihydropyridine-1(2H)-carboxylate (1.1 g, 2.30 mmol), and 10% palladium/carbon (0.1 g) in EtOAc (10 mL) was magnetically stirred under H₂ (50 psi). The progress of the reaction was monitored by GC/MS. The starting material disappeared within 5 h. The solid was filtered through a pad of Celite, and the organic phase was concentrated at reduced pressure to yield the title product (0.86 g, 78% yield).

Step 4: 2-(4-(piperidin-3-yl)phenyl-2,3,5,6-d₄)-2H-indazole-7-carboxamide

A procedure similar to that for Step 2 of Example 2 was used to synthesize the title compound from reaction of tert-butyl 3-(4-(7-(tert-butylcarbamoyl)-2H-indazol-2-yl)phenyl-2,3,5,6-d₄)piperidine-1-carboxylate (0.86 g, 1.79 mmol) with CH₃SO₃H (3.0 mL) and xylenes (2.0 mL). The resulting residue was purified by flash column (Combiflash RF+, DCM to 85% DCM/10% MeOH/5% NH₄OH) to afford the title compound as a powder (0.39 g, 67% yield). $^1$H NMR (300 MHz, DMSO-d₆): δ 9.28 (s, 1H), 8.58 (s, 1H), 8.08-8.01 (m, 2H), 7.89 (s, 1H), 7.27 (dd, J=7.5 Hz, 7.8 Hz, 1H), 3.08-3.03 (m, 2H), 2.72-2.51 (m, 2H), 1.94-1.90 (m, 1H), 1.73-1.49 (m, 4H). LCMS (Method A): m/z 325.2 ([M+H]$^+$), HPLC Rt 6.93 min.

Example 9

2-(4-(piperidin-3-yl-2,3-d₂)phenyl-2,3,5,6-d₄)-2H-indazole-7-carboxamide

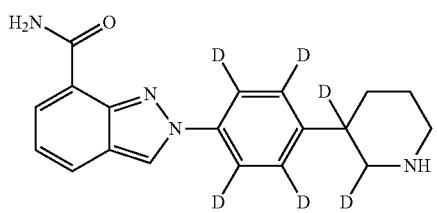 [SMILES: [2H]c1c([2H])c(C2([2H])CCCNC2[2H])c([2H])c([2H])c1-n1cc2cccc(C(N)=O)c2n1]

According to the procedures described in Example 8 (Scheme B), Example 9 was prepared from tert-butyl 3-(4-(7-(tert-butylcarbamoyl)-2H-indazol-2-yl)phenyl-2,3,5,6-d₄)piperidine-1-carboxylate-2,3-d₂ (0.65 g, 1.35 mmol) under conditions similar to Step 4 of Scheme B in Example 8 to afford 0.37 g (84% yield) of the title product. ¹H NMR (300 MHz, DMSO-d₆): δ 9.27 (s, 1H), 8.59 (s, 1H), 8.08-8.00 (m, 2H), 7.90 (s, 1H), 7.27 (dd, J=7.5 Hz, 7.8 Hz, 1H), 3.02-2.93 (m, 2H), 2.64-2.51 (m, 2H), 1.67-1.43 (m, 3H). LCMS (Method A): m/z 327.2 ([M+H]⁺), HPLC Rt 6.93 min.

Example 10

2-(4-(piperidin-3-yl-2,3-d₂)phenyl)-2H-indazole-7-carboxamide

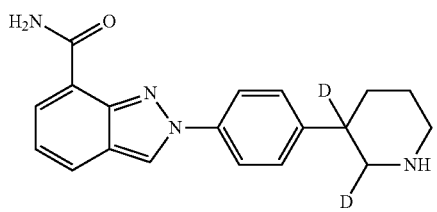 [SMILES: [2H]C1NCCCC1([2H])c1ccc(-n2cc3cccc(C(N)=O)c3n2)cc1]

According to the procedures described for Example 8, Example 10 was prepared from tert-butyl 3-(4-(7-(tert-butylcarbamoyl)-2H-indazol-2-yl)phenyl)piperidine-1-carboxylate-2,3-d₂ (2.6 g, 5.43 mmol) under conditions similar to Step 4 of Scheme B in Example 8 to afford 1.28 g (73% yield) of the title product. ¹H NMR (300 MHz, DMSO-d₆): δ 9.29 (s, 1H), 8.58 (s, 1H), 8.10-8.01 (m, 4H), 7.90 (s, 1H), 7.50 (d, J=8.4 Hz, 2H), 7.27 (dd, J=7.5 Hz, 7.8 Hz, 1H), 3.18-3.09 (m, 2H), 2.83-2.70 (m, 2H), 1.78-1.72 (m, 3H). LCMS (Method A): m/z 323.2 ([M+H]⁺), HPLC Rt 6.93 min.

Example 11

2-(4-(piperidin-3-yl)phenyl-2,3,5,6-d₄)-2H-indazole-3-d-7-carboxamide

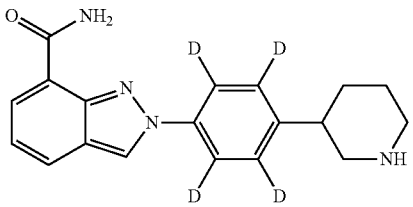 [SMILES: [2H]c1c([2H])c(-n2cc3cccc(C(N)=O)c3n2)c([2H])c([2H])c1C1CCCNC1]

According to the procedures described for Example 2, Example 11 was prepared from N-(tert-butyl)-1H-indazole-3-d-7-carboxamide (300 mg, 1.37 mmol, commercially available) and tert-butyl 3-(4-bromophenyl-2,3,5,6-d₄)piperidine-1-carboxylate under conditions similar to Steps 1 and 2 in Example 2 to afford 150 mg (34% yield) of the title product. m/z 326.2 ([M+H]⁺).

Example 12

2-(4-(piperidin-3-yl-2,3-d₂)phenyl)-2H-indazole-3-d-7-carboxamide

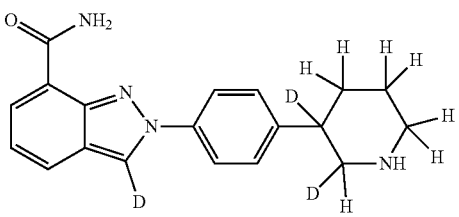 [SMILES: [2H]c1c2cccc(C(N)=O)c2nn1-c1ccc(C2([2H])CCCNC2[2H])cc1]

According to the procedures described for Example 2, 2-(4-(piperidin-3-yl-2,3-d₂)phenyl)-2H-indazole-3-d-7-carboxamide was prepared from N-(tert-butyl)-1H-indazole-3-d-7-carboxamide and tert-butyl 3-(4-bromophenyl)piperidine-1-carboxylate-2,3-d₂ under conditions similar to Steps 1 and 2 in Example 2 to afford of the 2-(4-(piperidin-3-yl-2,3-d₂)phenyl)-2H-indazole-3-d-7-carboxamide. m/z 324.2 ([M+H]⁺).

Example 13

(S)-2-(4-(piperidin-3-yl)phenyl)-2H-indazole-3-d-7-carboxamide

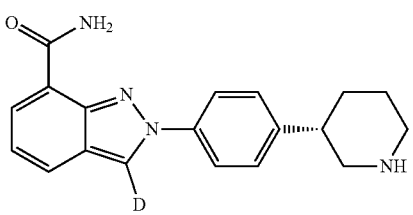 [SMILES: [2H]c1c2cccc(C(N)=O)c2nn1-c1ccc([C@@H]2CCCNC2)cc1]

Step 1: (S)-3-(4-bromophenyl)piperidine

N-Bromosuccinimide (800 mg, 4.5 mmol) was added to a solution of 0.96 g (5.96 mmol) of (S)-3-phenylpiperidine (commercially available) in 50% sulfuric acid (11 ml) and the mixture was stirred at 70° C. for 30 min. A saturated aqueous potassium carbonate solution was added to the solution while cooling with ice, and the mixture was extracted twice with diethyl ether. The organic layer was dried over anhydrous sodium sulfate, filtered, and then concentrated under the reduced pressure. The residue was purified by column chromatography on silica gel (chloroform:methanol:concentrated aqueous ammonia=9:0.6:0.06) to yield 1.0 g (yield 72%) of the crude title compound. MS (GC) m/z 239 M$^+$.

Step 2: tert-butyl (S)-3-(4-bromophenyl)piperidine-1-carboxylate

To a suspension of (S)-3-(4-bromophenyl)-piperidine (1.35 g, 5.62 mmol), and triethylamine (1.14 g, 11.2 mmol) in $CH_2Cl_2$ (13 mL) was added di-tert-butyl-dicarbonate (1.5 g, 6.74 mmol) at room temperature. After stirring for 15 h, the resulting suspension was partitioned between ethyl acetate and sodium hydroxide. The aqueous layer was extracted with ethyl acetate. The combined organic layer was washed with brine, dried over magnesium sulfate, and concentrated in vacuo. The residue was washed by hexane to furnish the product (S)-3-(4-bromophenyl)-piperidine-1-carboxylic acid tert-butyl ester as a solid.

Step 3: (S)-2-(4-(piperidin-3-yl)phenyl)-2H-indazole-3-d-7-carboxamide

According to the procedures described for Example 2, Example 13 was prepared from N-(tert-butyl)-1H-indazole-3-d-7-carboxamide (1.1 g, 5.0 mmol, commercially available) and tert-butyl (S)-3-(4-bromophenyl)piperidine-1-carboxylate (1.8 g, 5.3 mmol) under conditions similar to Steps 1 and 2 in Example 2 to afford 160 mg (10% yield) of the title product. LCMS (Method A): m/z 322.2 ([M+H]$^+$).

Example 14

(S)-2-(4-(piperidin-3-yl-2,2,3,4,4,5,5,6,6-d$_9$)phenyl)-2H-indazole-7-carboxamide

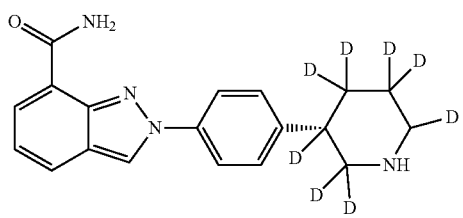 [SMILES: [2H]C1NC([2H])([2H])[C@]([2H])(c2ccc(-n3cc4cccc(C(N)=O)c4n3)cc2)C([2H])([2H])C1([2H])[2H]]

According to the literature procedure described in Jones, P. et al. *J. Med. Chem.* 2009, 52, 7170-85, separation of racemic 2-(4-(piperidin-3-yl-2,2,3,4,4,5,5,6,6-d$_9$)phenyl)-2H-indazole-7-carboxamide (Example 3) by chiral SFC yielded enantiomers (S)-2-(4-(piperidin-3-yl-2,2,3,4,4,5,5,6,6-d$_9$)phenyl)-2H-indazole-7-carboxamide and (R)-2-(4-(piperidin-3-yl-2,2,3,4,4,5,5,6,6-d$_9$)phenyl)-2H-indazole-7-carboxamide. The racemate was separated by chiral SFC purification using $CO_2$ as supercritical eluent: column, Chiralpak AS-H, 1 mm×25 mm; flow=10 mL/min; T$_{col}$=35° C.; P$_{col}$=100 bar; modifier, 55% $^i$PrOH containing 4% Et$_2$NH. The retention time of the first eluting enantiomer was 4.80 min. Evaporation of the solvent followed by lyophilization yielded (R)-2-(4-(piperidin-3-yl-2,2,3,4,4,5,5,6,6-d$_9$)phenyl)-2H-indazole-7-carboxamide as a white powder (ee>98.0%). The retention time of the second eluting enantiomer was 6.51 min. Evaporation of the solvent followed by lyophilization yielded (S)-2-(4-(piperidin-3-yl-2,2,3,4,4,5,5,6,6-d$_9$)phenyl)-2H-indazole-7-carboxamide as a white powder (ee>98%).

Example 15

(S)-2-(4-(piperidin-3-yl)phenyl-2,3,5,6-d$_4$)-2H-indazole-3-d-7-carboxamide

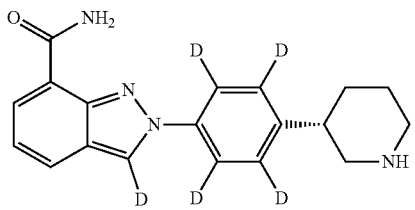 [SMILES: [2H]c1c([2H])c(-n2nc3c(C(N)=O)cccc3c2[2H])c([2H])c([2H])c1[C@@H]1CCCNC1]

According to the procedures described for Example 14, Example 15 was prepared from racemic 2-(4-(piperidin-3-yl)phenyl-2,3,5,6-d$_4$)-2H-indazole-3-d-7-carboxamide (400 mg, 1.23 mmol, Example 11) under conditions similar to Example 14 to afford 140 mg (35% yield) of the title product.

Microsomal Assays

In vitro liver metabolism studies have been described previously. See Obach, R. S. "Prediction of human clearance of twenty-nine drugs from hepatic microsomal intrinsic clearance data: An examination of in vitro half-life approach and nonspecific binding to microsomes," *Drug Metab. Disp.* 1999, 27, 1350; Houston, J. B. et al. "Prediction of hepatic clearance from microsomes, hepatocytes, and liver slices," *Drug Metab. Rev.* 1997, 29, 891; Houston, J. B. "Utility of in vitro drug metabolism data in predicting in vivo metabolic clearance," *Biochem. Pharmacol.* 1994, 47, 1469; Iwatsubo, T. et al. "Prediction of in vivo drug metabolism in the human liver from in vitro metabolism data," *Pharmacol. Ther.* 1997, 73, 147; Lave, T. et al. "The use of human hepatocytes to select compounds based on their expected hepatic extraction ratios in humans," *Pharm. Res.* 1997, 14, 152.

The studies described below in Examples 16-20 were performed to determine the metabolic stability of the test compounds in pooled liver microsomal incubations. Samples of the test compounds obtained from Examples 2-3, 5-9, and 15 above and racemic niraparib were exposed to pooled rat liver microsomes and then analyzed using UPLC LC-MS/MS detection.

The microsomal assay studies described below in Examples 16-20 were conducted according to the following experimental procedures:

1. Buffer solutions were prepared as follows:
   a. Buffer A: 0.1 M monobasic potassium phosphate buffer containing 1.0 mM EDTA.
   b. Buffer B: 0.1 M dibasic potassium phosphate buffer containing 1.0 mM EDTA.
   c. Buffer C: 0.1 M potassium phosphate buffer containing 1.0 mM EDTA was adjusted to pH 7.4 by titrating 700 mL of Buffer B with Buffer A while monitoring with a pH meter.
2. An NADPH stock solution (6 mM) was prepared by dissolving NADPH into Buffer C.
3. Spiking solutions were prepared for the reference compound (ketanserin) and the test compounds as follows:
   a. A 500 μM spiking solution of the reference compound (ketanserin) was generated by adding 10 μL of a 10 mM stock solution of ketanserin in DMSO into 190 μL acetonitrile. A 1.5 μM spiking solution in microsomes (0.75 mg/mL) was generated by adding 1.5 μL of the 500 μM spiking solution and 18.75 μL of 20 mg/mL rat liver microsomes into 479.75 μL of Buffer C while cooling with ice.
   b. For the test compounds, a 250 μM spiking solution was generated by adding 5 μL of 10 mM of a deuterated isotopologue of niraparib from one of Examples 2-3, 5-9, and 15 in DMSO; optionally adding 5 μL of 10 mM of a different deuterated isotopologue of niraparib from one of Examples 2-3, 5-9, and 15 in DMSO; and optionally 5 μL of 10 mM racemic niraparib in DMSO into 185 μL or 190 μL acetonitrile, where 185 μL of acetonitrile is used when three test compounds (niraparib and/or one or more of its isotopologues) are present and 190 μL acetonitrile is used when two test compounds (niraparib and/or one or more of its isotopologues) are present. A 0.75 μM spiking solution in microsomes (0.75 mg/mL) was generated by adding 1.5 μL of the 250 μM spiking solution and 18.75 μL of 20 mg/mL rat liver microsomes into 479.75 μL of Buffer C while cooling with ice.
4. 30 μL of 1.5 μM spiking solution containing 0.75 mg/mL microsomes solution was dispensed into assay plates designated for different time points (0 min, 5 min, 15 min, 30 min, and 45 min; or 0 min, 15 min, 30 min, 45 min, and 60 min as shown in Tables 1-5 below) while cooling with ice.
5. For the 0 min time point assay plate, 135 μL of ACN containing IS followed immediately by 15 μL of the 6 mM NADPH stock solution were added to the wells of the 0 min assay plate.
6. All assay plates other than the 0 min assay plate were pre-incubated at 37° C. for 5 min, and then 15 μL of the 6 mM NADPH stock solution was added to the wells of the assay plates to start the reaction and timing. At the appropriate time (5 min, 15 min, 30 min, 45 min, or 60 min), 135 μL of ACN containing IS was added to the wells of the corresponding assay plates, respectively, to stop the reaction.
7. After quenching, the plates were shaken in a vibrator (IKA, MTS 2/4) for 10 min (600 rpm/min) and then centrifuged at 5594 g for 15 min (Thermo Multifuge× 3R).
8. After centrifugation, 50 μL of the supernatant from each well was transferred into a 96-well sample plate containing 50 μL of ultrapure water (Millipore, ZMQS50F01) for LC/MS analysis.

Example 16

The compounds from Examples 2 and 3 were compared to racemic niraparib with respect to metabolic stability in a rat liver microsome assay.

TABLE 1

Metabolic Stability in Rat Liver Microsomes.

| Test Article | Species | | Percent Remaining (%) | | | | | | $T_{1/2}$ (min) | $Cl_{int}$ (mL/min/kg) |
| --- | --- | --- | --- | --- | --- | --- | --- | --- | --- | --- |
| | | | 0 min | 5 min | 15 min | 30 min | 45 min | 60 min | | |
| ketanserin | rat | mean | 100.00 | 65.84 | 41.07 | 17.68 | 9.13 | — | 13.20 | 188.09 |
| | | RSD of area ratio | 0.01 | 0.03 | 0.05 | 0.01 | 0.09 | — | | |
| racemic niraparib from mixture | rat | mean | 100.00 | — | 89.16 | 75.88 | 69.11 | 60.43 | 82.37 | 30.15 |
| | | RSD of area ratio | 0.06 | — | 0.01 | 0.01 | 0.07 | 0.01 | | |
| compound from Example 3 from mixture | rat | mean | 100.00 | — | 92.77 | 82.19 | 74.60 | 69.31 | 109.30 | 22.72 |
| | | RSD of area ratio | 0.06 | — | 0.03 | 0.03 | 0.06 | 0.04 | | |
| compound from Example 2 from mixture | rat | mean | 100.00 | — | 93.04 | 80.95 | 75.60 | 69.05 | 109.62 | 22.66 |
| | | RSD of area ratio | 0.03 | — | 0.01 | 0.01 | 0.05 | 0.02 | | |

The test compounds were evaluated in the rat liver microsome assay described above along with ketanserin as a positive control. The columns of Table 1 labeled "Percent Remaining" refer to the percentage of each test compound remaining after 0, 5, 15, 30, 45, and 60 min intervals in the rat liver microsome assay.

As shown in Table 1, the deuterated isotopologue from Example 3 displayed better stability over time with $T_{1/2}$ extended to 109.30 min as compared to 82.37 min for niraparib, providing a 32% increase in rat liver microsome metabolic stability as compared to niraparib.

As shown in Table 1, the deuterated isotopologue from Example 2 of the invention displayed appreciable stability over time with $T_{1/2}$ extended to 109.62 min as compared to 82.37 min for niraparib, providing a 33% increase in rat liver microsome metabolic stability as compared to niraparib.

As shown in Table 1, the deuterated isotopologue from Example 3 also displayed an appreciable clearance rate with $Cl_{int}$ reduced to 22.72 mL/min/kg from 30.15 mL/min/kg for niraparib.

As shown in Table 1, the deuterated isotopologue from Example 2 also displayed an appreciable clearance rate with $Cl_{int}$ reduced to 22.66 mL/min/kg from 30.15 mL/min/kg for niraparib.

Example 17

The compounds from Examples 6 and 7 were compared to racemic niraparib with respect to metabolic stability in a rat liver microsome assay.

TABLE 2

Metabolic Stability in Rat Liver Microsomes.

| Test Article | Species | | Percent Remaining (%) | | | | | $T_{1/2}$ (min) | $Cl_{int}$ (mL/min/kg) |
| --- | --- | --- | --- | --- | --- | --- | --- | --- | --- |
| | | | 0 min | 5 min | 15 min | 30 min | 45 min | | |
| ketanserin | rat | mean | 100 | 94.13 | 61.07 | 32.18 | 21.24 | 17.54 | 141.57 |
| | | RSD of area ratio | 0.07 | 0 | 0 | 0.03 | 0.05 | | |
| racemic niraparib from mixture | rat | mean | 100 | 116.67 | 95.83 | 83.18 | 81.48 | 101.67 | 24.43 |
| | | RSD of area ratio | 0.04 | 0.01 | 0.04 | 0.07 | 0.03 | | |
| compound from Example 7 from mixture | rat | mean | 100 | 112.62 | 94.47 | 84.9 | 83.06 | 117.75 | 21.09 |
| | | RSD f area ratio | 0.04 | 0.01 | 0.05 | 0.02 | 0.04 | | |
| compound from Example 6 from mixture | rat | mean | 100 | 112 | 100 | 88.27 | 85.02 | 132.26 | 18.78 |
| | | RSD of area ratio | 0.04 | 0 | 0.02 | 0.05 | 0.06 | | |

The test compounds were evaluated in the rat liver microsome assay described above along with ketanserin as a positive control. The columns of Table 2 labeled "Percent Remaining" refer to the percentage of each test compound remaining after 0, 5, 15, 30, and 45 min intervals in the rat liver microsome assay.

As shown in Table 2, the deuterated isotopologue from Example 7 displayed better stability over time with $T_{1/2}$ extended to 117.75 min as compared to 101.67 min for niraparib, providing a 16% increase in rat liver microsome metabolic stability as compared to niraparib.

As shown in Table 2, the deuterated isotopologue from Example 6 of the invention displayed appreciable stability over time with $T_{1/2}$ extended to 132.26 min as compared to 101.67 min for niraparib, providing a 30% increase in rat liver microsome metabolic stability as compared to niraparib.

As shown in Table 2, the deuterated isotopologue from Example 7 also displayed an appreciable clearance rate with $Cl_{int}$ reduced to 21.09 mL/min/kg from 24.43 mL/min/kg for niraparib.

As shown in Table 2, the deuterated isotopologue from Example 6 also displayed an appreciable clearance rate with $Cl_{int}$ reduced to 18.78 mL/min/kg from 24.43 mL/min/kg for niraparib.

Example 18

The compound from Example 5 was compared to racemic niraparib with respect to metabolic stability in a rat liver microsome assay.

TABLE 3

Metabolic Stability in Rat Liver Microsomes.

| Test Article | Species | | Percent Remaining (%) | | | | | | $T_{1/2}$ (min) | $Cl_{int}$ (mL/min/kg) |
| --- | --- | --- | --- | --- | --- | --- | --- | --- | --- | --- |
| | | | 0 min | 5 min | 15 min | 30 min | 45 min | 60 min | | |
| ketanserin | rat | mean | 100.00 | 78.33 | 45.04 | 21.55 | 10.67 | — | 13.87 | 179.11 |
| | | RSD of area ratio | 0.02 | 0.05 | 0.03 | 0.04 | 0.02 | — | | |
| racemic niraparib from mixture | rat | mean | 100.00 | — | 92.47 | 65.45 | 51.57 | 50.17 | 52.95 | 46.91 |
| | | RSD of area ratio | 0.10 | — | 0.12 | 0.03 | 0.42 | 0.07 | | |
| compound from Example 5 from mixture | rat | mean | 100.00 | — | 108.00 | 89.02 | 81.33 | 80.31 | 143.96 | 17.25 |
| | | RSD of area ratio | 0.02 | — | 0.06 | 0.12 | 0.03 | 0.00 | | |

The test compounds were evaluated in the rat liver microsome assay described above along with ketanserin as a positive control. The columns of Table 3 labeled "Percent Remaining" refer to the percentage of each test compound remaining after 0, 5, 15, 30, 45, and 60 min intervals in the rat liver microsome assay.

As shown in Table 3, the deuterated isotopologue from Example 5 displayed much better stability over time with $T_{1/2}$ extended to 143.96 min as compared to 52.95 min for niraparib, providing a 172% increase in rat liver microsome metabolic stability as compared to niraparib.

As shown in Table 3, the deuterated isotopologue from Example 5 also displayed an appreciable clearance rate with $Cl_{int}$ reduced to 17.25 mL/min/kg from 46.91 mL/min/kg for niraparib.

Example 19

The compounds from Examples 8 and 9 were compared to racemic niraparib with respect to metabolic stability in a rat liver microsome assay.

TABLE 4

Metabolic Stability in Rat Liver Microsomes.

| Test Article | | Species | Percent Remaining (%) | | | | | | $T_{1/2}$ (min) | $Cl_{int}$ (mL/min/kg) |
| --- | --- | --- | --- | --- | --- | --- | --- | --- | --- | --- |
| | | | 0 min | 5 min | 15 min | 30 min | 45 min | 60 min | | |
| ketanserin | rat | mean | 100.00 | 78.33 | 45.04 | 21.55 | 10.67 | — | 13.87 | 179.11 |
| | | RSD of area ratio | 0.02 | 0.05 | 0.03 | 0.04 | 0.02 | — | | |
| compound from Example 8 from mixture | rat | mean | 100.00 | — | 91.49 | 79.13 | 80.74 | 56.02 | 80.96 | 30.68 |
| | | RSD of area ratio | 0.21 | — | 0.00 | 0.19 | 0.12 | 0.07 | | |
| compound from Example 9 from mixture | rat | mean | 100.00 | — | 98.91 | 83.70 | 79.62 | 75.27 | 132.40 | 18.76 |
| | | RSD of area ratio | 0.10 | — | 0.29 | 0.00 | 0.18 | 0.08 | | |

The test compounds were evaluated in the rat liver microsome assay described above along with ketanserin as a positive control. The columns of Table 4 labeled "Percent Remaining" refer to the percentage of each test compound remaining after 0, 5, 15, 30, 45, and 60 min intervals in the rat liver microsome assay.

As shown in Table 4, the deuterated isotopologue from Example 9 displayed better stability over time with $T_{1/2}$ extended to 132.40 min as compared to 80.96 min for the deuterated isotopologue from Example 8, providing a 64% increase in rat liver microsome metabolic stability.

As shown in Table 4, the deuterated isotopologue from Example 9 also displayed an appreciable clearance rate with $Cl_{int}$ reduced to 18.76 mL/min/kg from 30.68 mL/min/kg for the deuterated isotopologue from Example 8.

Example 20

The compound from Example 15 was compared to racemic niraparib with respect to metabolic stability in a rat liver microsome assay.

TABLE 5

Metabolic Stability in Rat Liver Microsomes.

| Test Article | | Species | Percent Remaining (%) | | | | | | $T_{1/2}$ (min) | $Cl_{int}$ (mL/min/kg) |
| --- | --- | --- | --- | --- | --- | --- | --- | --- | --- | --- |
| | | | 0 min | 5 min | 15 min | 30 min | 45 min | 60 min | | |
| ketanserin | rat | mean | 100.00 | 82.83 | 51.29 | 25.82 | 15.08 | — | 16.15 | 153.75 |
| | | RSD of area ratio | 0.05 | 0.06 | 0.06 | 0.06 | 0.03 | — | | |
| racemic niraparib from mixture | rat | mean | 100.00 | — | 77.23 | 65.45 | 53.43 | 42.23 | 49.68 | 50.00 |
| | | RSD of area ratio | 0.04 | — | 0.04 | 0.01 | 0.04 | 0.07 | | |
| compound from Example 15 from mixture | rat | mean | 100.00 | — | 77.88 | 67.35 | 56.14 | 44.60 | 53.52 | 46.40 |
| | | RSD of area ratio | 0.04 | — | 0.00 | 0.01 | 0.02 | 0.06 | | |

The test compounds were evaluated in the rat liver microsome assay described above along with ketanserin as a positive control. The columns of Table 5 labeled "Percent Remaining" refer to the percentage of each test compound remaining after 0, 5, 15, 30, 45, and 60 min intervals in the rat liver microsome assay.

As shown in Table 5, the deuterated isotopologue from Example 15 displayed better stability over time with $T_{1/2}$ extended to 53.52 min as compared to 49.68 min for niraparib, providing a 8% increase in rat liver microsome metabolic stability as compared to niraparib.

As shown in Table 5, the deuterated isotopologue from Example 15 also displayed an appreciable clearance rate with $Cl_{int}$ reduced to 46.40 mL/min/kg from 50.00 mL/min/kg for niraparib.

The results of the microsomal assay studies indicate that the disclosed deuterated isotopologues of niraparib may exhibit beneficial properties as compared to niraparib when administered to patients, e.g., improved metabolic liability.

Anticancer Activity Screening

The studies described below in Examples 21-23 were performed to screen the disclosed compounds for anticancer activity. Samples of the test compounds obtained from Examples 3, 4, and 11 were screened for anticancer activity as described below.

The test compounds were screened for anticancer activity at the Development Therapeutic Program (DTP), National Cancer Institute (NCI), USA, against a full NCI 59 cell line panel (six cell lines of leukemia, nine cell lines of lung cancer, seven cell lines of colon cancer, six cell lines of CNS cancer, nine cell lines of melanoma, seven cell lines of ovarian cancer, seven cell lines of renal cancer, two cell lines of prostate cancer, and six cell lines of breast cancer) representing nine human systems in total as leukemia, melanoma, and cancers of the lungs, colon, brain, breast, ovary, kidney, and prostate, according to the applied protocol. A primary in vitro one dose anticancer assay was performed at a single dose (10 μM) against the full NCI 59 cell line panel. The one dose data was reported as a mean graph of the percent growth of treated cells. The number reported for the single dose assay was growth relative to the no drug control and relative to the initial number of cells at time 0. This allowed detection of both growth inhibition (values between 0 and 100) and lethality (values less than 0). For example, a value of 100 means no growth inhibition. A value of 40 means 60% growth inhibition. A value of 0 means no net growth over the course of the experiment. A value of −40 means 40% lethality. A value of −100 means all cells are dead.

Example 21

The compound from Example 11 was screened for anticancer activity against the full NCI 59 cell line panel described above. Results of the one dose assay for the compound from Example 11 are shown in Table 6.

TABLE 6

Results of NCI 59 Cell One-Dose Screen.

| PANEL NAME | CELL NAME | Growth Percentage |
|---|---|---|
| Leukemia | CCRF-CEM | 68.34 |
| Leukemia | HL-60(TB) | 69.13 |
| Leukemia | K-562 | 87.94 |
| Leukemia | MOLT-4 | 71.06 |

TABLE 6-continued

Results of NCI 59 Cell One-Dose Screen.

| PANEL NAME | CELL NAME | Growth Percentage |
|---|---|---|
| Leukemia | RPMI-8226 | 78.32 |
| Leukemia | SR | 37.42 |
| Non-Small Cell Lung Cancer | A549/ATCC | 70.16 |
| Non-Small Cell Lung Cancer | EKVX | 91.65 |
| Non-Small Cell Lung Cancer | HOP-62 | 94.55 |
| Non-Small Cell Lung Cancer | HOP-92 | 79.03 |
| Non-Small Cell Lung Cancer | NCI-H226 | 92.42 |
| Non-Small Cell Lung Cancer | NCI-H23 | 82.01 |
| Non-Small Cell Lung Cancer | NCI-H322M | 85.94 |
| Non-Small Cell Lung Cancer | NCI-H460 | 80.76 |
| Non-Small Cell Lung Cancer | NCI-H522 | 89.79 |
| Colon Cancer | COLO 205 | 79.11 |
| Colon Cancer | HCC-2998 | 80.10 |
| Colon Cancer | HCT-116 | 81.62 |
| Colon Cancer | HCT-15 | 85.76 |
| Colon Cancer | HT29 | 87.71 |
| Colon Cancer | KM12 | 83.99 |
| Colon Cancer | SW-620 | 72.01 |
| CNS Cancer | SF-268 | 82.89 |
| CNS Cancer | SF-295 | 90.94 |
| CNS Cancer | SF-539 | 77.48 |
| CNS Cancer | SNB-19 | 85.34 |
| CNS Cancer | SNB-75 | 76.35 |
| CNS Cancer | U251 | 92.89 |
| Melanoma | LOX IMVI | 71.49 |
| Melanoma | MALME-3M | 92.14 |
| Melanoma | M14 | 90.64 |
| Melanoma | MDA-MB-435 | 91.99 |
| Melanoma | SK-MEL-2 | 108.51 |
| Melanoma | SK-MEL-28 | 101.33 |
| Melanoma | SK-MEL-5 | 91.06 |
| Melanoma | UACC-257 | 102.12 |
| Melanoma | UACC-62 | 76.75 |
| Ovarian Cancer | IGROV1 | 74.29 |
| Ovarian Cancer | OVCAR-3 | 97.70 |
| Ovarian Cancer | OVCAR-4 | 103.47 |
| Ovarian Cancer | OVCAR-5 | 89.69 |
| Ovarian Cancer | OVCAR-8 | 84.66 |
| Ovarian Cancer | NCI/ADR-RES | 89.85 |
| Ovarian Cancer | SK-OV-3 | 94.12 |
| Renal Cancer | 786-0 | 97.43 |
| Renal Cancer | A498 | 83.22 |
| Renal Cancer | ACHN | 72.39 |
| Renal Cancer | RXF 393 | 107.27 |
| Renal Cancer | SN12C | 81.90 |
| Renal Cancer | TK-10 | 102.70 |
| Renal Cancer | UO-31 | 79.89 |
| Prostate Cancer | PC-3 | 68.67 |
| Prostate Cancer | DU-145 | 87.51 |
| Breast Cancer | MCF7 | 69.21 |
| Breast Cancer | MDA-MB-231/ATCC | 76.99 |
| Breast Cancer | HS 578T | 81.82 |
| Breast Cancer | BT-549 | 91.44 |
| Breast Cancer | T-47D | 90.97 |
| Breast Cancer | MDA-MB-468 | 87.13 |

The results indicate that the deuterated isotopologue from Example 11 significantly reduced the growth of the cell lines of leukemia SR (reduction to 37.42%), colon cancer SW-620 (reduction to 72.01%), ovarian cancer IGROV1 (reduction to 74.29%), and renal cancer ACHN (reduction to 72.39%).

Example 22

The compound from Example 4 was screened for anticancer activity against the full NCI 59 cell line panel described above. Results of the one dose assay for the compound from Example 4 are shown in Table 7.

TABLE 7

Results of NCI 59 Cell One-Dose Screen.

| PANEL NAME | CELL NAME | Growth Percentage |
| --- | --- | --- |
| Leukemia | CCRF-CEM | 89.50 |
| Leukemia | HL-60(TB) | 77.68 |
| Leukemia | K-562 | 77.76 |
| Leukemia | MOLT-4 | 78.10 |
| Leukemia | RPMI-8226 | 90.85 |
| Leukemia | SR | 47.47 |
| Non-Small Cell Lung Cancer | A549/ATCC | 67.08 |
| Non-Small Cell Lung Cancer | EKVX | 88.21 |
| Non-Small Cell Lung Cancer | HOP-62 | 86.84 |
| Non-Small Cell Lung Cancer | HOP-92 | 90.59 |
| Non-Small Cell Lung Cancer | NCI-H226 | 91.01 |
| Non-Small Cell Lung Cancer | NCI-H23 | 84.26 |
| Non-Small Cell Lung Cancer | NCI-H322M | 84.01 |
| Non-Small Cell Lung Cancer | NCI-H460 | 76.94 |
| Non-Small Cell Lung Cancer | NCI-H522 | 87.37 |
| Colon Cancer | COLO 205 | 82.07 |
| Colon Cancer | HCC-2998 | 83.97 |
| Colon Cancer | HCT-116 | 77.22 |
| Colon Cancer | HCT-15 | 84.17 |
| Colon Cancer | HT29 | 77.66 |
| Colon Cancer | KM12 | 87.65 |
| Colon Cancer | SW-620 | 72.23 |
| CNS Cancer | SF-268 | 89.52 |
| CNS Cancer | SF-295 | 85.63 |
| CNS Cancer | SF-539 | 82.30 |
| CNS Cancer | SNB-19 | 88.53 |
| CNS Cancer | SNB-75 | 70.09 |
| CNS Cancer | U251 | 83.63 |
| Melanoma | LOX IMVI | 70.64 |
| Melanoma | MALME-3M | 79.53 |
| Melanoma | M14 | 84.68 |
| Melanoma | MDA-MB-435 | 92.97 |
| Melanoma | SK-MEL-2 | 101.94 |
| Melanoma | SK-MEL-28 | 98.37 |
| Melanoma | SK-MEL-5 | 91.65 |
| Melanoma | UACC-257 | 107.99 |
| Melanoma | UACC-62 | 85.29 |
| Ovarian Cancer | IGROV1 | 73.75 |
| Ovarian Cancer | OVCAR-3 | 107.53 |
| Ovarian Cancer | OVCAR-4 | 98.64 |
| Ovarian Cancer | OVCAR-5 | 89.23 |
| Ovarian Cancer | OVCAR-8 | 82.86 |
| Ovarian Cancer | NCI/ADR-RES | 84.74 |
| Ovarian Cancer | SK-OV-3 | 90.49 |
| Renal Cancer | 786-0 | 92.79 |
| Renal Cancer | A498 | 89.03 |
| Renal Cancer | ACHN | 72.83 |
| Renal Cancer | RXF 393 | 102.74 |
| Renal Cancer | SN12C | 89.59 |
| Renal Cancer | TK-10 | 96.15 |
| Renal Cancer | UO-31 | 75.43 |
| Prostate Cancer | PC-3 | 85.40 |
| Prostate Cancer | DU-145 | 89.54 |
| Breast Cancer | MCF7 | 64.30 |
| Breast Cancer | MDA-MB-231/ATCC | 80.47 |
| Breast Cancer | HS 578T | 86.01 |
| Breast Cancer | BT-549 | 99.58 |
| Breast Cancer | T-47D | 98.04 |
| Breast Cancer | MDA-MB-468 | 86.59 |

The results indicate that the deuterated isotopologue from Example 4 significantly reduced the growth of the cell lines of leukemia SR (reduction to 47.47%), ovarian cancer IGROV1 (reduction to 73.75%), and breast cancer MCF7 (reduction to 64.30%).

Example 23

The compound from Example 3 was screened for anticancer activity against the full NCI 59 cell line panel described above. Results of the one dose assay for the compound from Example 3 are shown in Table 8.

TABLE 8

Results of NCI 59 Cell One-Dose Screen.

| PANEL NAME | CELL NAME | Growth Percentage |
| --- | --- | --- |
| Leukemia | CCRF-CEM | 87.92 |
| Leukemia | HL-60(TB) | 89.31 |
| Leukemia | K-562 | 89.73 |
| Leukemia | MOLT-4 | 86.53 |
| Leukemia | RPMI-8226 | 87.86 |
| Leukemia | SR | 59.44 |
| Non-Small Cell Lung Cancer | A549/ATCC | 67.74 |
| Non-Small Cell Lung Cancer | EKVX | 100.49 |
| Non-Small Cell Lung Cancer | HOP-62 | 93.86 |
| Non-Small Cell Lung Cancer | HOP-92 | 98.72 |
| Non-Small Cell Lung Cancer | NCI-H226 | 93.61 |
| Non-Small Cell Lung Cancer | NCI-H23 | 91.99 |
| Non-Small Cell Lung Cancer | NCI-H322M | 98.96 |
| Non-Small Cell Lung Cancer | NCI-H460 | 86.91 |
| Non-Small Cell Lung Cancer | NCI-H522 | 83.10 |
| Colon Cancer | COLO 205 | 94.82 |
| Colon Cancer | HCC-2998 | 88.49 |
| Colon Cancer | HCT-116 | 83.66 |
| Colon Cancer | HCT-15 | 100.98 |
| Colon Cancer | HT29 | 93.28 |
| Colon Cancer | KM12 | 99.34 |
| Colon Cancer | SW-620 | 84.69 |
| CNS Cancer | SF-268 | 88.94 |
| CNS Cancer | SF-295 | 96.74 |
| CNS Cancer | SF-539 | 96.82 |
| CNS Cancer | SNB-19 | 91.61 |
| CNS Cancer | SNB-75 | 76.50 |
| CNS Cancer | U251 | 85.78 |
| Melanoma | LOX IMVI | 76.95 |
| Melanoma | MALME-3M | 91.23 |
| Melanoma | M14 | 98.03 |
| Melanoma | MDA-MB-435 | 98.88 |
| Melanoma | SK-MEL-2 | 117.90 |
| Melanoma | SK-MEL-28 | 107.36 |
| Melanoma | SK-MEL-5 | 93.38 |
| Melanoma | UACC-257 | 97.56 |
| Melanoma | UACC-62 | 84.84 |
| Ovarian Cancer | IGROV1 | 83.23 |
| Ovarian Cancer | OVCAR-3 | 103.07 |
| Ovarian Cancer | OVCAR-4 | 106.31 |
| Ovarian Cancer | OVCAR-5 | 100.56 |
| Ovarian Cancer | OVCAR-8 | 81.93 |
| Ovarian Cancer | NCI/ADR-RES | 97.76 |
| Ovarian Cancer | SK-OV-3 | 96.60 |
| Renal Cancer | 786-0 | 103.31 |
| Renal Cancer | A498 | 90.94 |
| Renal Cancer | ACHN | 77.21 |
| Renal Cancer | RXF 393 | 111.56 |
| Renal Cancer | SN12C | 93.25 |
| Renal Cancer | TK-10 | 98.41 |
| Renal Cancer | UO-31 | 80.19 |
| Prostate Cancer | PC-3 | 80.86 |
| Prostate Cancer | DU-145 | 97.89 |
| Breast Cancer | MCF7 | 75.22 |
| Breast Cancer | MDA-MB-231/ATCC | 83.62 |
| Breast Cancer | HS 578T | 86.68 |
| Breast Cancer | BT-549 | 113.02 |
| Breast Cancer | T-47D | 98.94 |
| Breast Cancer | MDA-MB-468 | 109.78 |

The results indicate that the deuterated isotopologue from Example 3 significantly reduced the growth of the cell lines of leukemia SR (reduction to 59.44%), non-small cell lung cancer A549/ATCC (reduction to 67.74%), melanoma cancer LOX IMVI (reduction to 76.95%), ovarian cancer OVCAR-8 (reduction to 81.93%), renal cancer ACHN (reduction to 77.21%), and breast cancer MCF7 (reduction to 75.22%).

The previous description of the disclosed embodiments is provided to enable any person skilled in the art to make or use the invention disclosed herein. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

All references cited herein are expressly incorporated by reference.

What is claimed is:

1. A compound of Formula (I):

$$(I)$$

or a pharmaceutically acceptable salt thereof;
wherein $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ are selected from the group consisting of hydrogen and deuterium, and wherein at least one of $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ is deuterium.

2. The compound of claim 1, wherein $Y^9$, $Y^{9'}$, $Y^{10}$, $Y^{10'}$, $Y^{11}$, $Y^{11'}$, $Y^{12}$, $Y^{12'}$, and $Y^{13}$ are each deuterium, and wherein $Y^1$, $Y^2$, $Y^3$, $Y^4$, $Y^5$, $Y^6$, $Y^7$, and $Y^8$ are each hydrogen.

3. The compound of claim 1, wherein $Y^9$, $Y^{10}$, $Y^{11}$ and $Y^{12}$ are each deuterium, and wherein $Y^1$, $Y^2$, $Y^3$, $Y^4$, $Y^5$, $Y^6$, $Y^7$, $Y^8$, $Y^{9'}$, $Y^{10'}$, $Y^{11'}$, $Y^{12'}$, and $Y^{13}$ are each hydrogen.

4. The compound of claim 1, wherein $Y^9$, $Y^{10'}$, $Y^{11'}$, $Y^{12}$ and $Y^{13}$ are each deuterium, and wherein $Y^1$, $Y^2$, $Y^3$, $Y^4$, $Y^5$, $Y^6$, $Y^7$, $Y^8$, $Y^{9'}$, $Y^{10'}$, $Y^{11'}$, and $Y^{12'}$ are each hydrogen.

5. The compound of claim 1, wherein $Y^9$ and $Y^{13}$ are each deuterium, and wherein $Y^1$, $Y^2$, $Y^3$, $Y^4$, $Y^5$, $Y^6$, $Y^7$, $Y^8$, $Y^{9'}$, $Y^{10}$, $Y^{10'}$, $Y^{11}$, $Y^{11'}$, $Y^{12}$, and $Y^{12'}$ are each hydrogen.

6. The compound of claim 1, wherein $Y^4$ is a deuterium, and wherein $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ are each hydrogen.

7. The compound of claim 1, wherein $Y^5$, $Y^6$, $Y^7$, and $Y^8$ are each deuterium, and wherein $Y^1$, $Y^2$, $Y^3$, $Y^4$, $Y^9$, $Y^{9'}$, $Y^{10}$, $Y^{10'}$, $Y^{11}$, $Y^{11'}$, $Y^{12}$, $Y^{12'}$, and $Y^{13}$ are each hydrogen.

8. The compound of claim 1, wherein $Y^5$, $Y^6$, $Y^7$, $Y^8$, $Y^9$, and $Y^{13}$ are each deuterium, and wherein $Y^1$, $Y^2$, $Y^3$, $Y^4$, $Y^{9'}$, $Y^{10}$, $Y^{10'}$, $Y^{11}$, $Y^{11'}$, $Y^{12}$, and $Y^{12'}$ are each hydrogen.

9. The compound of claim 1, wherein $Y^5$, $Y^6$, $Y^7$, $Y^8$, $Y^9$, $Y^{10}$, $Y^{11}$, and $Y^{12}$ are each deuterium, and wherein $Y^1$, $Y^2$, $Y^3$, $Y^4$, $Y^{9'}$, $Y^{10'}$, $Y^{11'}$, $Y^{12'}$, and $Y^{13}$ are each hydrogen.

10. The compound of claim 1, wherein $Y^5$, $Y^6$, $Y^7$, $Y^8$, $Y^9$, $Y^{10}$, $Y^{11}$, $Y^{12}$, and $Y^{13}$ are each deuterium, and wherein $Y^1$, $Y^2$, $Y^3$, $Y^4$, $Y^{9'}$, $Y^{10'}$, $Y^{11'}$, and $Y^{12'}$ are each hydrogen.

11. The compound of claim 1, wherein $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ are each deuterium, and wherein $Y^1$, $Y^2$, $Y^3$, and $Y^4$ are each hydrogen.

12. The compound of claim 1, wherein $Y^4$, $Y^5$, $Y^6$, $Y^7$, and $Y^8$ are each deuterium, and wherein $Y^1$, $Y^2$, $Y^3$, $Y^9$, $Y^{9'}$, $Y^{10}$, $Y^{11}$, $Y^{11'}$, $Y^{12}$, $Y^{12'}$, and $Y^{13}$ are each hydrogen.

13. The compound of claim 1, wherein $Y^4$, $Y^9$, $Y^{9'}$, $Y^{10}$, $Y^{10'}$, $Y^{11}$, $Y^{11'}$, $Y^{12}$, $Y^{12'}$, and $Y^{13}$ are each deuterium, and wherein $Y^1$, $Y^2$, $Y^3$, $Y^5$, $Y^6$, $Y^7$, and $Y^8$ are each hydrogen.

14. The compound of claim 1, wherein $Y^4$, $Y^9$, $Y^{10}$, $Y^{11}$, and $Y^{12}$ are each deuterium, and wherein $Y^1$, $Y^2$, $Y^3$, $Y^5$, $Y^6$, $Y^7$, $Y^8$, $Y^{9'}$, $Y^{10'}$, $Y^{11'}$, $Y^{12'}$, and $Y^{13}$ are each hydrogen.

15. The compound of claim 1, wherein $Y^4$ and $Y^{13}$ are each deuterium, and wherein $Y^1$, $Y^2$, $Y^3$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, and $Y^{12'}$ are each hydrogen.

16. The compound of claim 1, wherein $Y^4$, $Y^9$, and $Y^{13}$ are each deuterium, wherein $Y^1$, $Y^2$, $Y^3$, $Y^5$, $Y^6$, $Y^7$, $Y^8$, $Y^{9'}$, $Y^{10}$, $Y^{10'}$, $Y^{11}$, $Y^{11'}$, $Y^{12}$, and $Y^{12'}$ are each hydrogen.

17. The compound of claim 1, wherein $Y^{13}$ is a deuterium, and wherein $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, and $Y^{12'}$ are each hydrogen.

18. The compound of claim 1, wherein $Y^1$, $Y^2$, $Y^3$, $Y^4$, $Y^5$, $Y^6$, $Y^7$, $Y^8$, $Y^9$, $Y^{9'}$, $Y^{10}$, $Y^{10'}$, $Y^{11}$, $Y^{11'}$, $Y^{12}$, $Y^{12'}$, and $Y^{13}$ are each deuterium.

19. A pharmaceutical composition comprising the compound of claim 1 and a pharmaceutically acceptable carrier.

* * * * *